United States Patent
Seely

(10) Patent No.: US 8,473,306 B2
(45) Date of Patent: Jun. 25, 2013

(54) METHOD AND APPARATUS FOR MONITORING PHYSIOLOGICAL PARAMETER VARIABILITY OVER TIME FOR ONE OR MORE ORGANS

(75) Inventor: Andrew J. E. Seely, Ottawa (CA)

(73) Assignee: Ottawa Hospital Research Institute, Ottawa (CA)

(*) Notice: Subject to any disclaimer, the term of this patent is extended or adjusted under 35 U.S.C. 154(b) by 527 days.

(21) Appl. No.: 12/752,902

(22) Filed: Apr. 1, 2010

(65) Prior Publication Data

US 2010/0261977 A1 Oct. 14, 2010

Related U.S. Application Data

(63) Continuation of application No. PCT/CA2008/001720, filed on Oct. 1, 2008.

(60) Provisional application No. 60/977,179, filed on Oct. 3, 2007.

(51) Int. Cl.
*G06Q 10/00* (2012.01)
*G06Q 50/00* (2012.01)

(52) U.S. Cl.
USPC .................. 705/2; 705/3; 600/300

(58) Field of Classification Search
USPC .................. 340/870–77; 600/300
See application file for complete search history.

(56) References Cited

U.S. PATENT DOCUMENTS

| | | |
|---|---|---|
| 4,510,944 A | 4/1985 | Porges |
| 5,042,497 A | 8/1991 | Shapland |
| 5,105,354 A | 4/1992 | Nishimura |
| 5,309,920 A | 5/1994 | Gallant et al. |
| 5,438,983 A | 8/1995 | Falcone |
| 5,447,164 A | 9/1995 | Shaya et al. |
| 5,579,775 A | 12/1996 | Dempsey et al. |
| 5,609,770 A | 3/1997 | Zimmerman et al. |

(Continued)

FOREIGN PATENT DOCUMENTS

| | | |
|---|---|---|
| CA | 2408502 A1 | 11/2001 |
| CA | 2418003 A1 | 1/2002 |

(Continued)

OTHER PUBLICATIONS

Brun-Buisson, C.; "The epidemiology of the systemic inflammatory response"; Intensive Care Med; 2000; 26: S64 to S74; Springer-Verlag.

(Continued)

*Primary Examiner* — Michelle Le
(74) *Attorney, Agent, or Firm* — Brett J. Slaney; Blake, Cassels & Graydon LLP

(57) ABSTRACT

A system is provided for leveraging the power of the analysis of variability over time, and which uses an underlying framework that can handle variability analyses across a distributed system in a consistent manner, in part by constructing a standard variability data file that includes several manifestations of the underlying data acquired using variability monitoring. The consistent and standard data files, along with the underlying framework enables a user to make use of a set of convenient display tools, while a central entity can provide connectivity to the distributed environment and provide a way to update the equipment and software to ensure consistent and relevant analyses. The system can be extended into many environments, including in-patient, out-patient and completely mobile/stand-alone users.

48 Claims, 25 Drawing Sheets

U.S. PATENT DOCUMENTS

| | | | |
|---|---|---|---|
| 5,664,270 | A | 9/1997 | Bell et al. |
| 5,771,897 | A | 6/1998 | Zufrin |
| 5,816,247 | A | 10/1998 | Maynard |
| 5,917,415 | A | 6/1999 | Atlas |
| 6,050,951 | A | 4/2000 | Friedman et al. |
| 6,144,878 | A | 11/2000 | Schroeppel et al. |
| 6,212,427 | B1 | 4/2001 | Hoover |
| 6,216,032 | B1 | 4/2001 | Griffin et al. |
| 6,301,499 | B1 | 10/2001 | Carlson et al. |
| 6,305,943 | B1 | 10/2001 | Pougatchev et al. |
| 6,356,775 | B1 | 3/2002 | Kondo et al. |
| 6,361,503 | B1 | 3/2002 | Starobin et al. |
| 6,409,659 | B1 | 6/2002 | Warner et al. |
| 6,480,733 | B1 | 11/2002 | Turcott |
| 6,558,321 | B1 | 5/2003 | Burd et al. |
| 6,600,949 | B1 | 7/2003 | Turcott |
| 6,773,396 | B2 | 8/2004 | Flach et al. |
| 6,835,176 | B2 | 12/2004 | McNair |
| 6,858,006 | B2 | 2/2005 | MacCarter et al. |
| 6,876,303 | B2 | 4/2005 | Reeder et al. |
| 7,031,857 | B2 | 4/2006 | Tarassenko et al. |
| 7,038,595 | B2 | 5/2006 | Seely |
| 7,079,888 | B2 | 7/2006 | Oung et al. |
| 7,258,667 | B2 | 8/2007 | McNair |
| 7,307,102 | B2 | 12/2007 | McDonnell et al. |
| 7,324,845 | B2 | 1/2008 | Mietus et al. |
| 8,170,887 | B2 * | 5/2012 | Rosenfeld et al. ............ 705/2 |
| 2002/0183976 | A1 | 12/2002 | Pearce |
| 2002/0192624 | A1 | 12/2002 | Darby et al. |
| 2003/0107487 | A1 | 6/2003 | Korman et al. |
| 2003/0117296 | A1 | 6/2003 | Seely |
| 2003/0163057 | A1 * | 8/2003 | Flick et al. ............... 600/509 |
| 2003/0232795 | A1 | 12/2003 | McDonnell et al. |
| 2004/0111033 | A1 | 6/2004 | Oung et al. |
| 2005/0027205 | A1 | 2/2005 | Tarassenko et al. |
| 2005/0192488 | A1 | 9/2005 | Bryenton et al. |
| 2006/0122474 | A1 | 6/2006 | Teller et al. |
| 2006/0264730 | A1 | 11/2006 | Stivoric et al. |
| 2007/0021675 | A1 | 1/2007 | Childre et al. |
| 2007/0069887 | A1 | 3/2007 | Welch et al. |
| 2007/0073181 | A1 | 3/2007 | Pu et al. |

FOREIGN PATENT DOCUMENTS

| | | |
|---|---|---|
| CA | 2627386 A1 | 9/2008 |
| WO | WO 99/47040 A1 | 9/1999 |
| WO | WO 2006/094055 A2 | 9/2006 |
| WO | WO 2007/149856 A2 | 12/2007 |

OTHER PUBLICATIONS

Angust, Derek C.; et al.; "Epidemiology of severe sepsis in the United States: Analysis of incidence, outcome, and associated costs of care"; Crit Care Med. 2001; Jul. 2001; pp. 1303 to 1310; vol. 20, No. 7.

Regazzoni, Carlos J. et al.; "Neutropenia and the development of the systemic inflammatory response syndrome"; Intensive Care Med; Jan. 2003; 29(1); pp. 135 to 138.

Gallagher, R.; Appenzeller T.; "Beyond Reductionism"; Science; Apr. 2, 1999; vol. 284, No. 5411 p. 79.

Weinberg, C.R.; "An Improved Method for Measuring Heart-Rate Variability: Assessment of Cardiac Autonomic Function"; Biometrics 40; Sep. 1984; pp. 855 to 861.

Seeley, Andrew J.E. et al.; "Multiple organ dysfunction syndrome: Exploring the paradigm of complex nonlinear systems"; Crit Care Med; 2000; pp. 2193 to 2200; vol. 28, No. 7.

Seeley, Andrew J.E.; et al.; "Complex Systems and the Technology of Variability Analysis"; Critical Care; Dec. 2004; vol. 8, No. 6.

The Ansar Group Home page; http://www.ans-hrv.com/; online at least as early as May 7, 2010.

Clinicians Vicor Technologies, Inc.; "Vicor's PD2i® Nonlinear Algorithm—An overview"; http://www.vicortech.com/clinicians_overview.htm.; online at least as early as May 7, 2010.

Neth, O.W. et al.; "Susceptibility to infection in patients with neutropenia: the role of the innate immune system"; Jun. 2005; British Journal of Haematology; 129(6); pp. 713 to 722; Blackwell Publishing Ltd.

Siddiqui, Imran; International Search Report from PCT Application No. PCT/CA2008/001720; search completed Jan. 19, 2009.

Philips, Petra; Supplementary Search Report from corresponding European Application No. 08800404.9; search completed Oct. 10, 2012.

* cited by examiner

METHOD AND APPARATUS FOR MONITORING PHYSIOLOGICAL PARAMETER VARIABILITY OVER TIME FOR ONE OR MORE ORGANS

CROSS-REFERENCE TO RELATED APPLICATIONS

This application is a continuation of International PCT Application No. PCT/CA2008/001720 filed on Oct. 1, 2008 which claims priority from U.S. Provisional Patent Application No. 60/977,179 filed on Oct. 3, 2007, the contents of which are hereby incorporated by reference.

TECHNICAL FIELD

The following relates generally to medical monitoring and has particular utility in monitoring of physiological parameter variability over time for one or more organs.

BACKGROUND

Bacterial infection remains a major cause of suffering and death, particularly in patients with impaired host defence. Although there is extensive knowledge on the mechanisms, pathways, mediators, transcription factors, receptor levels and gene activation involved in the host response to severe infection, which may lead to organ dysfunction, the understanding of the whole system working in concert typically has limitations.

In the clinical setting, current monitoring techniques have achieved a high level of sophistication, involving vital sign monitoring, labs, and a variety of radiology, microbiology and pathology tests. Although these tests are generally adequate to reliably diagnose infection, the criteria to diagnose infection are non-specific. Frequently, a gestalt of individually non-specific clinical signs and symptoms lead to the diagnosis of infection and initiation of antibiotic therapy. As such, the timing of diagnosis is imprecise, insensitive and subject to judgement, which may lead to delay. In certain patient populations with increased susceptibility or impaired reserve, the delay in diagnosis, even if measured in hours, may prove catastrophic. Clinical deterioration may be well underway prior to recognition and response. Late diagnosis of infection, rapid clinical deterioration, ICU admission and organ dysfunction are not uncommon in the case histories of critically ill patients.

For example, severe sepsis and septic shock are the most common causes of mortality in critically ill patients, accounting for 10% of intensive care unit admissions (Brun-Buisson C. The epidemiology of the systemic inflammatory response. Intensive Care Med. 2000; 26 Suppl 1:S64-74) and 2.9% of all hospital admissions (Angus D C, Linde-Zwirble W T, Lidicker J, Clermont G, Carcillo J, Pinsky M R. Epidemiology of severe sepsis in the United States: analysis of incidence, outcome, and associated costs of care. Crit. Care Med. 2001 July; 29(7):1303-10). Given the proven benefit of early resuscitation in sepsis, there is additional imperative to develop methods to diagnose infection earlier with potential to save lives.

In another example, neutropenia is an intended iatrogenic side effect of myeloablative chemotherapy, commonly employed in the management of malignant hematological diseases, most commonly leukemia and lymphoma. Consequently, the host's immune system is compromised leading to increasing risk of opportunistic infections (Neth O W, Bajaj-Elliott M, Turner M W, Klein N J. Susceptibility to infection in patients with neutropenia: the role of the innate immune system. Br J. Haematol. 2005 June; 129(6):713-22). Febrile illness during neutropenia is often the first indication of infection. It requires prompt antimicrobial therapy with possible hospitalization. Thus, depending on therapy, neutropenic patients experience a variable risk of fever, but when fever occurs, it is synonymous with infection in the majority of patients.

Prognosis of neutropenic infection is largely dictated by the severity of the systemic inflammatory response syndrome (SIRS) and clinical progression to sepsis syndrome, severe septic shock and organ failure, with increasing risk of death. Overall, febrile neutropenic patients admitted to the intensive care unit with systemic inflammatory response syndrome display a mortality risk of 20%, increasing to 90% in the presence of septic shock (Regazzoni C J, Khoury M, Irrazabal C, Myburg C, Galvalisi N R, O'Flaherty M, et al. Neutropenia and the development of the systemic inflammatory response syndrome. Intensive Care Med. 2003 January; 29(1):135-8) Regression analysis demonstrated that mortality was not modified by age, malignancy or positive blood cultures, highlighting the importance of the host response in determining outcome. These results underscore the importance of early diagnosis and early identification of severity of illness in the management of febrile neutropenic patients.

Complex systems are systems comprised of a dynamic web of a large and variably interconnected number of elements. Arising from the complex interconnection of the parts (e.g. bees, neurons) and their environment (i.e. non-equilibrium), a new entity called a complex system (e.g. beehive, CNS) arises possessing distinct systemic or emergent properties (e.g. capacity to make honey, cognition, memory). Given that systemic properties are wholly distinct from the properties of the parts, complex systems cannot be fully understood solely by understanding their parts, no matter how thorough that understanding may be (Gallagher R, Appenzeller T. Beyond Reductionism. Science. 1999; 284:79) Given convincing evidence as well as promising insights, it has been observed that the host response to severe infection or injury, which may lead to organ dysfunction, is indeed a complex non-linear system (Seely A J, Christou N V. Multiple organ dysfunction syndrome: exploring the paradigm of complex nonlinear systems. Crit. Care Med. 2000 July; 28(7):2193-200).

Identifying the host response to severe insult as a complex system helps explain why unpredictable rapid deterioration in patients with infection and unexpected clinical improvement with no identifiable cause, both occur frequently, as uncertainty and surprise are ubiquitous within complex systems. If critical illness is characterized by an altered and unpredictable complex systemic response, then there is an imperative to monitor the whole system as a whole and do so over time, in order to track the trajectory of the system. As temporal variability of the parts is produced from the integrity and complexity of the whole system, then it has been hypothesized that continuous monitoring of variability offer means to monitor the whole system over time (Seely and Christou).

The science of characterizing rhythms, referred to most commonly as variability analysis, represents the means by which a time-series of a biologic signal is comprehensively characterized, utilizing an array of linear and non-linear variability analysis techniques based upon non-linear dynamics, chaos theory and mathematical physics (Seely A J, Macklem P T. Complex systems and the technology of variability analysis. Crit. Care. 2004 December; 8(6):R367-84). Each technique provides different and complementary means to characterize patterns of variation. Within a complex systems paradigm, variability analysis offers technology to more directly monitor the underlying system producing the dynamics.

A variety of techniques exist to quantify and characterize variation over time, including Time Domain, Frequency Domain, Entropy, and Scale-Invariant Analyses. Briefly, Time Domain analysis involves the raw data measured over time, an analysis of overall variation (standard deviation and range) and the degree to which data may be fit by standardized distributions (e.g. normal, log-normal). Frequency Domain analysis evaluates the frequency spectrum of a signal observed over time. Any time series may be represented as a sum of regular oscillations with distinct frequencies, conversion from a time domain to a frequency domain analysis (and back) is made possible with a mathematical transformation called the Fourier transform. Wavelet Analysis combines time and frequency domain variation information, providing a hybrid of time- and frequency-domain analysis. Entropy Analysis provides a measure of the degree of information, irregularity, disorder or complexity within a biologic signal. Mathematical calculations produce single (e.g. approximate or sample entropy) or multiple values (e.g. multiscale entropy) that reflect degree of irregularity or complexity. Scale-invariant Analysis provides a measure of common patterns of variation present across all time scales.

This panel of variability analysis techniques was developed to help characterize biologic signals. They have been applied to heart rate, respiratory rate, blood pressure, neutrophil count, temperature and more; investigations have consistently demonstrated the following: (1) patterns of variability provide additional clinically useful information regarding the absolute value of that parameter, (2) altered variation is present in association with age and illness, and (3) degree of alteration correlates with severity of illness.

A reduction in heart rate variability (HRV) has long been utilized as a means to identify fetal distress, as well as a marker of mortality risk in adult patients with heart disease. More recently, HRV evaluation has been performed in the presence of infection, demonstrating reproducible alteration in HRV in patients with sepsis, septic shock and organ dysfunction. Of value to intensivists, the degree to which HRV is altered in the presence of infection correlates with severity of illness. The results of many recent studies strongly support the hypothesis that altered HRV provides an untapped means of early identification of infection in adults.

In another environment, Multiple Organ Dysfunction Syndrome (MODS), defined by having two or more failing organ systems, is the clinical syndrome characteristic of the chronically, critically ill patients. MODS is the leading cause of mortality in intensive care unit (ICU) patients. MODS represents the sequential deterioration of organ function, usually leading to death, occurring in patients who are on the most advanced ICU life support technology possible. These patients require considerable human and hospital resources, including invasive monitoring in an ICU, one-on-one nursing, multiple transfusions, ventilators, dialysis, cardiac assist devices, vasopressors and more.

Evaluation of variability of patient parameters has only recently come under investigation in medical science, and is generally not used in routine clinical practice. As discussed above, variability describes the degree and character to which a parameter fluctuates over time. It is a principal component of the dynamics of a variable, which refers to its pattern of change over time. A parameter may be relatively constant, demonstrating a low degree of variability, or wildly fluctuate with high variability, or demonstrate decreased irregularity or complexity, or decreased high frequency variability.

Generally, reduced variability and complexity are correlated with illness state, however, both increased and decreased variability of individual patient parameters are associated with disease states. The positive clinical significance of the evaluation of these individual variables indicates that the evaluation of multiple patient parameters will provide for clinically useful information.

U.S. Pat. No. 7,038,595 to Seely, published May 2, 2006, describes a system for multiple patient parameter variability analysis and display. The system described in Seely, provides analysis and display of the variability of multiple patient parameters monitored by bedside monitors for each patient over time. Each monitored patient parameter is measured in real-time, data artefacts can be removed, and variability analysis is performed based upon a selected period of observation. Variability analysis of each interval of time yields variability of the patient parameters, which represents a degree to which the patient parameters change over an interval time, to provide diagnostic information particularly useful in the detection, prevention, and treatment of MODS among other uses.

Although such a system provides clinicians with variability data of multiple patient parameters simultaneously, along with the capability for variability analysis over time, there as yet exists no complete solution for organizing use of the acquired data, in particular aside from configurations in the ICU environment, or for conveniently handling data from multiple acquisition sites.

SUMMARY

It has been recognized that the change in variability over time, which can correlate with illness state, can be more conveniently displayed by providing additional variability display tools that enable a user to manipulate generic displays of variability data acquired over a plurality of intervals, in a configurable display toolkit. It has also been recognized that using a consistent variability data file for each variable (e.g. each organ), and combining the variability data files with corresponding waveform data files and other data pertaining to the user or patient enables deployment of a distributed framework that can acquire variability data for a plurality of time intervals through multiple sites concurrently obtaining each data with a separate variability analysis apparatus capable of monitoring one or more variables (e.g. organs). It has also been recognized that such a distributed framework enables software and operational updates as well as threshold information to be distributed to the multiple sites by a central service thus providing a consistent and standardized approach to conducting variability analyses.

Given that altered variability has been demonstrated in patients with infection, and correlation with severity of organ failure, the following system for conducting variability analyses over time through a distributed framework, is designed to enable early diagnosis of infection and real-time prognosis of organ failure.

In one aspect, there is provided a method for supporting variability analyses conducted over time at a plurality of sites, each variability analysis comprising computing a measure of variability for a plurality of time intervals for one or more parameters, each measure of variability indicative of a degree and character to which a respective parameter changes over an interval of time, the method comprising: providing a connection between a central service and the plurality of sites; the central service obtaining from each of the plurality of sites, a data package comprising one or more data files representing results of one or more variability analyses conducted at a respective one of the plurality of sites; the central service storing the data packages in a central database and making the database available for further processing; the central service providing threshold data to at least one of the plurality of sites, the threshold data comprising information pertaining to parameters of the variability analyses and being derived from the contents of the central database; and the central service providing update data to at least one of the plurality of sites, the update data comprising information for maintaining consistency among the operation of the plurality of sites.

In another aspect, there is provided a method for supporting variability analyses conducted over time at a plurality of sites, each variability analysis comprising computing a measure of variability for a plurality of time intervals for one or more parameters, each measure of variability indicative of a degree and character to which a respective parameter changes over an interval of time, for each of the plurality of sites, the method comprising: providing a connection between the site and a central service; preparing a data package comprising one or more data files representing results of one or more variability analyses conducted at the site; making the data package available to the central service to enable the central service to store the data package with other data packages in a central database and to make the database available for further processing; obtaining from the central service, threshold data comprising information pertaining to parameters of the variability analyses and being derived from the contents of the central database; and obtaining from the central service, update data comprising information for maintaining consistency of the site with others of the plurality of sites.

In yet another aspect, there is provided a method for supporting variability analyses conducted over time at a plurality of sites, each variability analysis comprising computing a measure of variability for a plurality of time intervals for one or more parameters, each measure of variability indicative of a degree and character to which a respective parameter changes over an interval of time, the method comprising: providing a connection between a central service and the plurality of sites; each of the plurality of sites preparing a data package comprising one or more data files representing results of one or more variability analyses conducted at a respective site; the plurality of sites making the data packages available to the central service; the central service obtaining from each of the plurality of sites, a data package comprising one or more data files; the central service storing the data packages in a central database and making the database available for further processing; the central service providing threshold data, the threshold data comprising information pertaining to parameters of the variability analyses and being derived from the contents of the central database; the plurality of sites obtaining the threshold data from the central service; the central service providing update data, the update data comprising information for maintaining consistency among the operation of the plurality of sites; and the plurality of sites obtaining the update data from the central service.

In yet another aspect, there is provided a method for preparing a data package representing results of one or more variability analyses conducted at a respective site over time, each variability analysis comprising computing a measure of variability for a plurality of time intervals for one or more parameters, each measure of variability indicative of a degree and character to which a respective parameter changes over an interval of time, the method comprising: obtaining a waveform for a parameter over a period of time comprising the plurality of time intervals; using the waveform to obtain raw sensor data comprising a raw time series; smoothing the raw sensor data to obtain smooth sensor data; using the smooth sensor data to conduct a variability analysis to obtain raw variability data; smoothing the raw variability data to obtain smooth variability data; associating time stamp data with the raw sensor data, the smooth sensor data, the raw variability data, and the smooth variability data; generating a variability data file using the raw sensor data, the smooth sensor data, the raw variability data, the smooth variability data, and the time stamp data; and including the variability data file in the data package.

In yet another aspect, there is provided a method for performing variability analyses conducted over time, each variability analysis comprising computing a measure of variability for a plurality of time intervals for one or more parameters, each measure of variability indicative of a degree and character to which a respective parameter changes over an interval of time, the method comprising: obtaining clinical events recorded during the variability analysis; associating one or more time stamps with the clinical events for correlating with data obtained during the variability analysis; and associating the clinical events in a data package representing results of one or more variability analyses for the one or more parameters.

In yet another aspect, there is provided a system for recording clinical events detected during variability analyses conducted over time, each variability analysis comprising computing a measure of variability for a plurality of time intervals for one or more parameters, each measure of variability indicative of a degree and character to which a respective parameter changes over an interval of time, the system comprising an event recorder for capturing the clinical events, the event recorder comprising a display for providing an interface for a user, and a computer readable medium comprising computer executable instructions for obtaining clinical events recorded during the variability analysis; and associating one or more time stamps with the clinical events for correlating with data obtained during the variability analysis.

In yet another aspect, there is provided a system for displaying data obtained during variability analyses conducted over time, each variability analysis comprising computing a measure of variability for a plurality of time intervals for one or more parameters, each measure of variability indicative of a degree and character to which a respective parameter changes over an interval of time, the system comprising a display toolkit and a data storage device for storing the data, the display toolkit being embodied as a computer readable medium having computer executable instructions for displaying time series data extracted from sensor data along with variability data associated with the time series data in the same screen.

It will be appreciated that these methods may be implemented as computer executable instructions on a computer readable medium and various systems may be configured to operate according to the methods as described below.

BRIEF DESCRIPTION OF THE DRAWINGS

An embodiment of the invention will now be described by way of example only with reference to the appended drawings wherein:

FIG. 24 is an output display showing an example interface for entering clinical events associated with a variability analysis.

FIG. 25 is an output display showing an example interface for selecting a variability analysis type.

DETAILED DESCRIPTION OF THE DRAWINGS

It has been recognized that the underlying theory behind the analysis of variability over multiple intervals of time (e.g. continuous variability analysis) has a widespread application in many environments, e.g. for treatment, early diagnosis and overall health monitoring.

It has also been recognized that the analysis of variability over time allows for various clinical applications. One such clinical application is the evaluation of a patient's own variability, that is the individualized change in variability that is detected by monitoring variability over multiple intervals of time. As will be explained below, the evaluation of a patient's variability has many uses, e.g. in detecting the onset of disease, both in real-time and retrospectively. Another such clinical application is the evaluation of change in variability in response to an intervention. For example, this enables the system described below, and/or parts thereof, to assist clinicians in the safety and timing of liberation from medical apparatus such as mechanical ventilation in critically ill patients.

In order to take advantage of the power of variability analysis over time for the above reasons and many more, an underlying framework has been developed that can handle multiple variability analyses over multiple intervals of time, across a distributed system in a consistent manner. This is accomplished, in part, by constructing and storing a standard waveform data file as well as a separate variability data file for each variable being analyzed, that includes a comprehensive characterization of the underlying data acquired using variability monitoring. The consistent and standard data files, along with the underlying framework enables a user to make use of a set of convenient variability display tools, while a central entity can provide connectivity to the distributed environment and provide a way to update the equipment and software to ensure consistent and relevant analyses. The system can be extended into many environments, including in-patient, out-patient and completely mobile/stand-alone.

Figure 1:
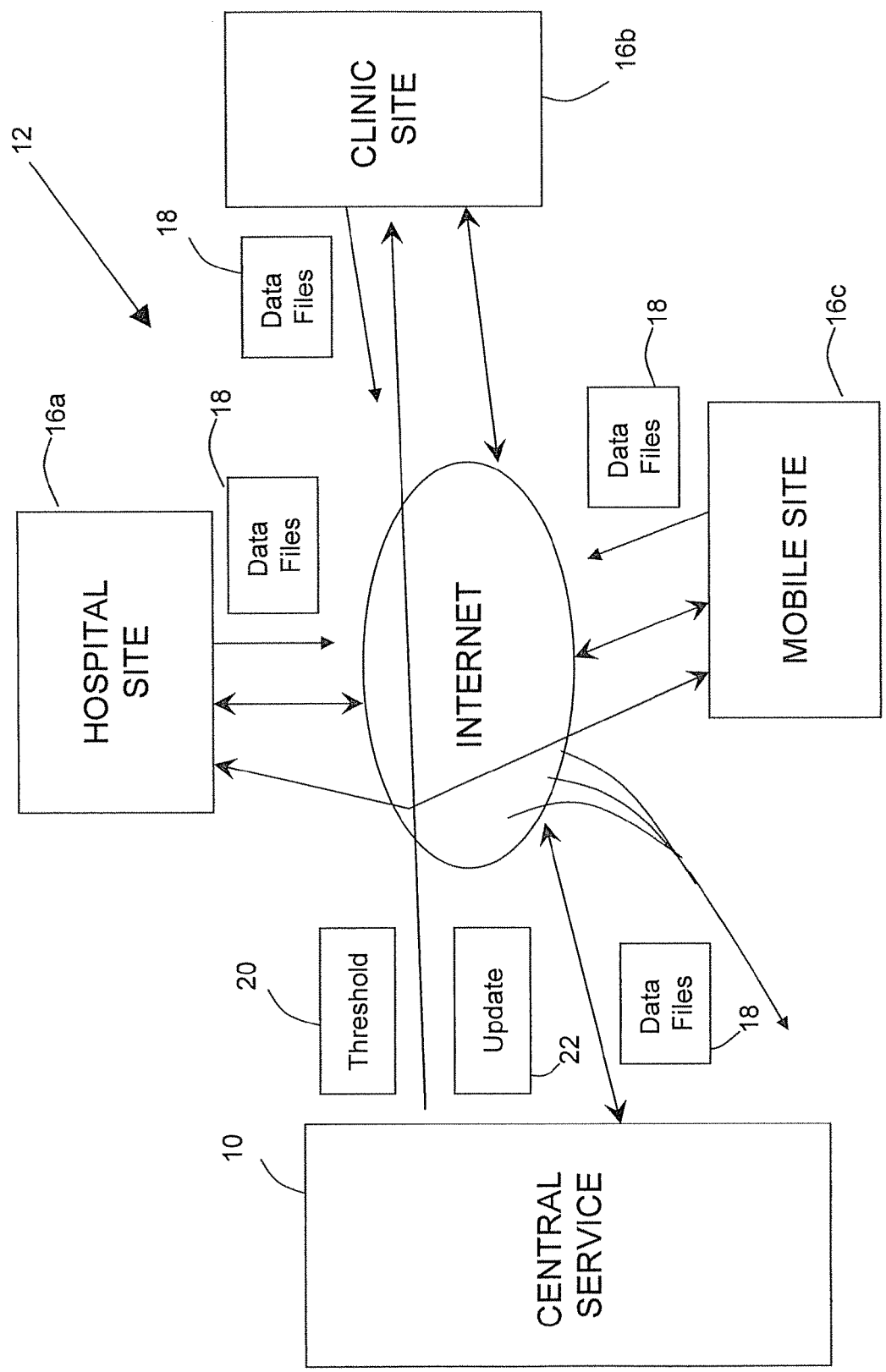
FIG. 1 is a schematic block diagram showing a centralized service for handling data acquired from one or more variability analysis monitoring sites.

Turning now to the figures, in particular FIG. 1, a central service 10 for obtaining, handling and processing data packages 18 obtained from one or more variability analysis monitoring sites 16 is shown, the monitoring sites 16 which obtain measurement data and perform an analysis of the variability of one or more parameters over multiple intervals of time to generate the data packages 18. It will be appreciated that a "variability analysis over time" or a "variability analysis" in general, will hereinafter refer to the computation of a measure of variability for a plurality of time intervals for each patient parameter, variable, organ etc. Each measure of variability is indicative of a degree and character to which a respective patient parameter changes over an interval of time, and each variability analysis enables changes in variability of the patient parameter to be observed over a period of time. A variability analysis as herein described can be performed on one or more patient parameters, i.e. single parameter and/or multi-parameter (e.g. single-organ or multi-organ), and the multiple measures of variability can be obtained according to any suitable pattern such as intermittent, continuous, etc.

The service 10 is part of a distributed data file management system 12, which also includes or makes use of a interconnection medium or network, in this example the Internet 14, and one or more variability analysis monitoring sites 16. In this example, three monitoring sites 16a-16c are shown, each having a different role in a different environment. Shown in this example is a hospital monitoring site 16a, a clinic site 16b and a mobile site 16c, each of which are explained in greater detail below.

There may be any number of monitoring sites 16 of any type (i.e. 16a, b or c) in any combination using any topology as required by the overall system 12. As such, the provision of three sites 16, one of each type, is shown for illustrative purposes only. Moreover, it will be appreciated that the network 14 can be any network, whether is be a local area network (LAN), wide area network (WAN), etc. providing wireless or wired access/communication in any suitable configuration. In this example, the Internet 14 is a particularly suitable medium for providing the connectivity between the central service 10, and the monitoring sites 16 such that many geographical locations can be accommodated, however, any other medium or intermediary would suffice, including direct connections in, e.g. a closed system. Examples might include a network of ICUs located anywhere in the world, or a network of bone marrow transplant centers. Each network has an individualized embodiment for performing single or multi-organ variability analyses, suited to its own needs.

As shown in FIG. 1, the Internet 14 provides a medium for transferring data between the central service 10 and the monitoring sites 16. Data packages 18 that are created at the monitoring sites 16 can be uploaded to the central service 10 by the monitoring sites 16 as shown, or may also be downloaded or 'pulled' from the monitoring sites 16 by the central service 10, e.g. using a periodic poll, transfer or batch process. In either case, the data packages 18 are of a suitable format to be transferred over the intermediary network, e.g. one or more data packets, email attachments, streaming data, etc., when using the Internet 14. The data packages 18 may also be text files, or a combination of several file types such as text, graphics, audio etc. It will be appreciated that the data packages 18 need not be embodied as discrete portions or packets during transmission but instead may be sent as continuous or semi-continuous data streams that are received and processed at the central service 10. Accordingly, it can be seen that the data packages 18 shown in FIG. 1 represent generally the flow of data from the monitoring sites 16 to the central service 10 and any network or signal provides a computer readable medium for carrying the data represented by the data packages 18. As will be explained further below, each data package 18 generally represents a particular transmission of data comprising one or more sets of a variability data file 103 and corresponding waveform data file 104, each set being associated with a particular parameter. It will be appreciated that the term "organ" is used herein for illustrative purposes only and may represent any parameter, variable, feature or item for which the analysis of variability over time can be measured.

Two other types of data transfers are also shown in FIG. 1, namely for threshold data 20 and update or upgrade data 22. The threshold data 20 contains information pertaining to the various thresholds that may be used by the monitoring sites 16 when conducting a variability analysis and to determine when alerts should be sounded. In variability analysis, a threshold represents the distinction between physiology and pathology that are specific to distinct patient populations as well as for distinct clinical applications. In other words, e.g., thresholds may differ for bone marrow transplant patients when compared to post operative patients or those admitted with congestive heart failure. As will be explained in greater detail below, the threshold data 20 is typically based on an amalgamation of data that has been obtained from multiple patients or users across the entire distributed system 12, which enables different thresholds to be identified for different clinical environments and patient populations. As such, the threshold data 20 offers a more complete look into the effects of variability and ways to look at the results of a variability analysis that would otherwise not be available without the configuration and connectivity shown in FIG. 1.

In addition, there may be methods used by which the variability data is amalgamated, creating an overall determination of pathology versus physiology.

The update data 22 contains upgrades, updates and any other useful information that is needed to maintain consistency across the entire system 12. As such, the connectivity in FIG. 1 also enables a consistent and standardized way in which variability analysis can be performed, in addition to the collaboration of data offered by the threshold data 20. It can thus be seen that the configuration and connectivity provided by the system 12 shown in FIG. 1 enables the central service 10 to maintain control over the quality and consistency of the variability analyses being performed at all the connected monitoring sites 16. Also, by gathering the data packages 18 from all monitoring sites 16, the central service 10 has access to a wider range of results for providing useful information not only as feedback by way of the threshold data 20 and updates 22, but also for research and/or learning as will be explained below. It will be appreciated that the threshold data 20 and update data 22 can possess similar characteristics as the data packages 18 and thus such details need not be reiterated.

Figure 2:
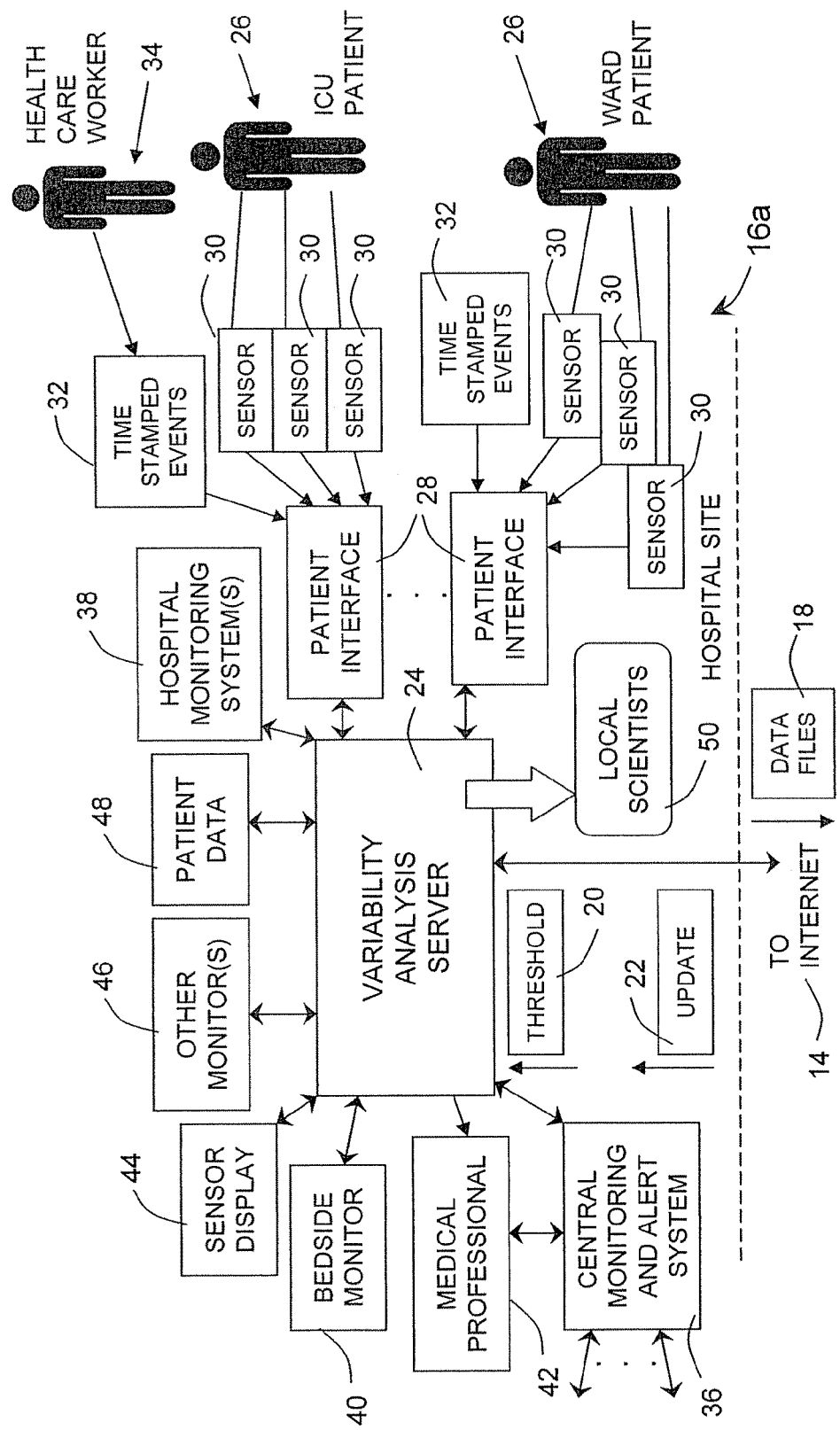
FIG. 2 is a schematic block diagram of the hospital site shown in FIG. 1.

An example of a hospital monitoring site 16a is shown in FIG. 2. The elements shown in FIG. 2 are meant to illustrate several possible components that may interact with one another at the hospital site 16a, however, any number (or all) of these elements can be used or not used in specific hospital sites 16a depending on the actual equipment and/or personnel present at the hospital site 16a and the needs of the patients 26 and personnel. In addition, the parameters being monitored (and the monitors themselves) may differ from network to network. As will be explained, at each monitoring site 16, including the hospital site 16a shown in FIG. 2, is at least one variability analysis server 24 for using acquired data to conduct variability analyses over time and generate data packages 18 that can be viewed at the site and provided to the central service 10. However, as shown, each variability analysis server 24 can interface with multiple patients 26 and, as such, typically only one variability analysis server 24 is required at each monitoring site 16. The variability analysis server 24 gathers data acquired from one or more patients 26 through individual patient interfaces 28, computes the measures of variability (i.e. conducts variability analyses) for one or more patient parameters, and connects to the central server 10 through the Internet 14 for facilitating the transfer and/or receipt of data packages 18, threshold data 20 and update data 22. As shown, there can be different types of patients 26 such as those in the ICU or in a regular hospital ward.

The patient interfaces 28 monitor physiological parameters of the patient 26 using one or more sensors 30. The data or patient parameters can include any variable that can be accurately measured in real time or intermittently. The data may be obtained from a continuous waveform (at a certain frequency level, e.g. 100 Hz for a CO2 capnograph or 500 Hz for an EKG), or taken as absolute measurements at certain intervals, e.g. temperature measurements. The sensors 30 and patient interfaces 28 may include, for example, an electrocardiogram (ECG), a $CO_2$ capnograph, a temperature sensor, a proportional assist ventilator, an optoelectronic plethymography, a urometer, a pulmonary arterial catheter, an arterial line, an $O_2$ saturation device and others. To provide more meaning to the data acquired through the sensors 30, clinical events are associated with the data, through an act of recording time stamped events 32, which are typically entered by a heath care worker 34 in the hospital (bedside) environment. Clinical (time stamped) events can be physical activity, administration of medication, diagnoses, life support, washing, rolling over, blood aspiration etc. The clinical events are associated with a specific time, which is then also associated with the data that is acquired at the same specific time using the sensors 30. It will be appreciated that the clinical events can also be recorded in an automated fashion, e.g. by utilizing algorithms which detect events electronically and process such events to designate them as clinical events or noise. In this example, the patient interface 28 is configured to gather the time stamped event data 32 concurrently with the sensor data 30, further detail being provided below. It may be noted that additional non-time-stamped information (e.g. demographics) can also be recorded for each patient.

As can be seen in FIG. 2, the variability analysis server 24 not only connects to the patient interfaces 28 and the Internet 14, but also to several other components/entities within the hospital site 16a. For example, the server 24 can interface with a hospital monitoring system 38 such as a nurse's station, as well as a central monitoring and alert system 36. The central monitoring and alert system 36 is capable of monitoring the variability analyses performed by the variability analysis server 24 in order to detect critical or potentially critical situations evident from such variability analyses and provide an alert or alerts to a medical professional 42, who can also receive data directly from the variability analysis server 24. The variability analysis server 24 can be embodied as a fixed unit or a moveable unit such as on a cart, in order to facilitate movement about the hospital site 16a to serve multiple patients 26 in multiple locations. Similarly, the variability analysis server 24 can be a proprietary apparatus or can be embodied as an add-on to existing beside or centralized equipment to minimize space.

The variability analysis server 24 can also interact with a bedside monitor 40, which may be made available to or otherwise represent a nurse or other personnel that monitors the patient 26 at the bedside. Similarly, the variability analysis server 24 can also interact with sensor displays 44, which are associated with other medical equipment such as ECGs, blood pressure sensors, temperature sensors etc. As noted above, the variability analysis server 24 can be a separate, stand-alone unit but may also be integrated as a plug-in or additional module that in this case could be used or integrated with existing bedside monitoring equipment, displays and sensors. FIG. 2 also shows other monitors 46 which can include any other monitoring system or equipment that either can provide useful medical data or patient data or would benefit from the data acquired by the variability analysis server 24. Patient data 48, e.g. provided by an electronic patient database (not shown) or manually entered can also interact with the variability analysis server 24. As will be discussed below, the patient data 48 may be appended to, or included with the data packages 18 to provide further context for the data contained therein. This enables patient specifics such as age, general health, sex etc. be linked to the acquired data to assist in organizing data into demographics. As also shown in FIG. 2, the variability analysis server 24 can provide data or otherwise useful information for local scientists 50 that are interested in or involved in the implications and effects of variability. It will be appreciated that patient privacy and other concerns can be addressed as required, by adding data security or other de-identification measures.

Figure 3:
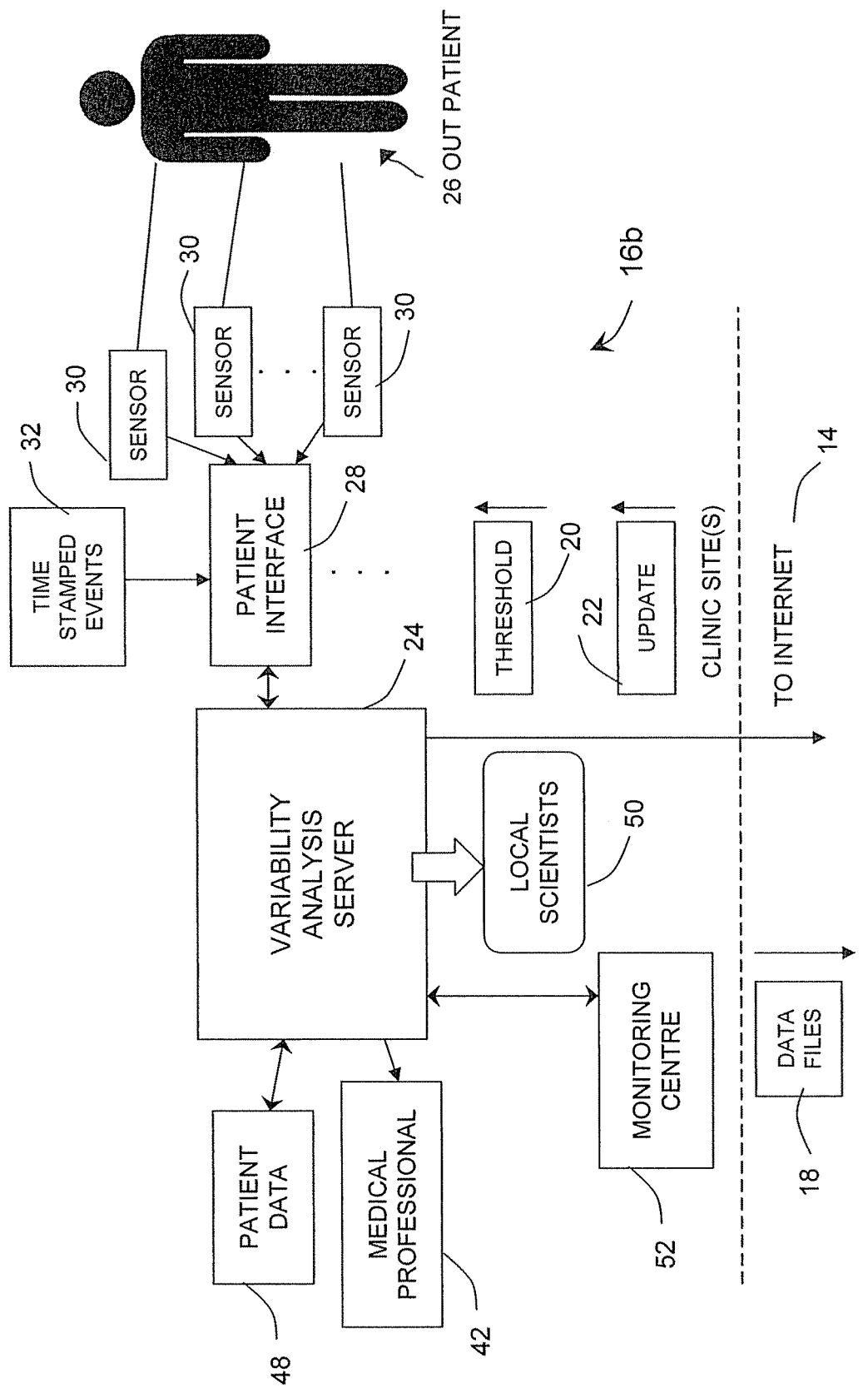
FIG. 3 is a schematic block diagram of the clinic site shown in FIG. 1.

Turning now to FIG. 3, a clinic site 16b is shown. An example of a clinic site 16b is a bone marrow transplant clinic. Similar to the hospital site 16a discussed above, the clinic site 16b includes a variability analysis server 24, that obtains data from one or more patient interfaces 28, and connects to the Internet 14 for facilitating data transfer (i.e. to send data packages 18 and to receive threshold data 20 and update data 22). In the clinic site 16b, the patients 26 are referred to as outpatients as they are not admitted to a hospital. The sensors 30, clinical events recorded as time stamped events 32 and patient data 48 is acquired and used in a manner similar to that discussed above and thus further details need not be reiterated. Similarly, the variability analysis server 24 can provide data and interact with medical professionals 42 at the clinic site 16b, as well as local scientists 50, if applicable. The clinic site 16b may include one or more variability analysis servers 24, and would typically include a monitoring centre 52 that monitors the analyses of the various outpatients 26 and provides alerts if necessary. The monitoring centre 52 enables the clinic's variability analysis server 24 to be monitored from a remote location and allows personnel to monitor several servers 24 if several are present in the clinic. In this way, a central monitoring centre 52 can be used to service several clinic sites 16b.

Figure 4:
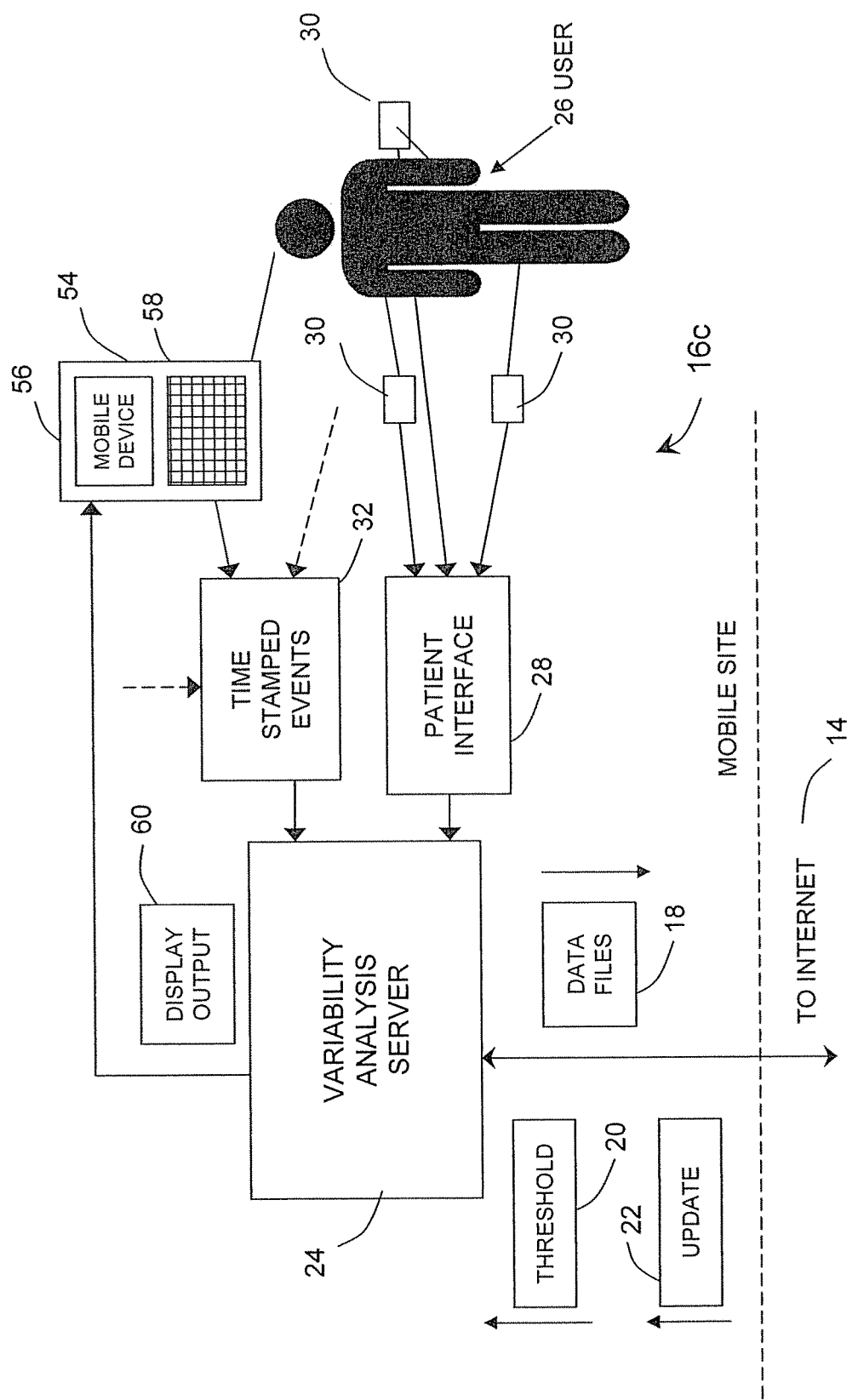
FIG. 4 is a schematic block diagram of the mobile site shown in FIG. 1.

A mobile site 16c is shown in FIG. 4. The mobile site 16c enables the capabilities of the variability analysis server 24 to be used outside of the hospital and clinical environments and, as such, in this embodiment, the mobile site 16c serves any "user" or "subject". For the sake of consistency, hereinafter the term "patient" will refer collectively to any user or subject. In this way, it may be appreciated that variability analyses can be performed on any user, including athletes, firefighters, police officers, or any other person that can benefit from monitoring variability of one or more physiological parameters. This can therefore extend to providing real-time monitoring in extreme environments such as during a fire, in a mine, during rescue missions etc. where variability can indicate a potentially critical situation. In all cases, variability can be monitored over time and analyzed on an individual basis for any patient 26 such that the resultant data is specific to that individual. Using the wider system 12 allows the central service 10 to take advantage of the individual results for many patients 26 and ascertain further and more complete information. The mobile site 16c generally represents any site that includes a variability analysis server 24, which connects to the central service 10 and can communicate with one or more patients 26, whether they are patients in the traditional sense or another type of user.

In the example shown in FIG. 4, the user 26 generally includes a mobile device 54 and has a number of sensors 30 that are in communication with a variability analysis server 24. The mobile device 54 can also be used to provide inputs, e.g. for the time stamped event data 32, as well as to provide a display to the user 26 for entering parameters or to view display data 60 acquired by the sensors 30 and/or processed by the server 24. The connections between the mobile device 54 and the server 24, as well as between the sensors 30 and patient interface 28 can be wired or wireless and the variability analysis server 24 can be a fixed unit at a base station or a portable unit such as on a cart at a monitoring centre. The mobile device 54 can be a personal digital assistant (PDA), mobile telephone, laptop computer, personal computer or any other device that can provide an input device, a display and some form of connectivity for interacting with the variability analysis server 24, preferably in a completely mobile manner.

As noted above, each monitoring site 16 includes a variability analysis server 24. Details of various embodiments of existing variability analysis apparatus and configurations can be found in U.S. Pat. No. 7,038,595 to Seely, the contents of which are incorporated herein by reference. As will be explained below in connection with FIGS. 5 and 6, the apparatus shown in Seely can be modified to work within the system 12 by adding functionality and features for gathering, displaying and transferring data, using a consistent procedure and consistent formats. First, the following provides further detail and examples regarding the acquisition of data by the sensors 30 and the patient interface 28.

Data acquisition involves the sequential recording of consecutive data for each of the patient parameters under investigation. Examples include: continuously recording cardiovascular parameter data; continuously recording respiratory parameter data; and recording other patient parameters at specified time intervals (e.g. glucose levels every 30 minutes).

As noted above, the data acquired for the variability analyses can be acquired from a continuous waveform, from which a time series can be sampled; or taken intermittently as absolute measurements.

Patient parameters may be grouped into organ systems to facilitate patient-monitoring and intervention. Table 1 shows patient parameters grouped by organ system and the parameters in italicized font represent those that are taken from a waveform.

TABLE 1

Patient Parameters
Variability Parameters by Organ System

| Cardiovascular | Respiratory | Renal | Liver | CNS |
|---|---|---|---|---|
| Heart Rate | Respiratory Rate | Urine Output | Arterial | EEG |
| Blood Pressure | $O_2$ Saturation | [Creatinine] | pH | [Glucose] |
| Cardiac Output | Arterial $pO_2$ | | lactate | $HCO_3$ |
| CVP | Arterial $pCO_2$ | | | [LDH] |
| $MVO_2$ | Impedance* | | | |
| SVR | Compliance* | | | |
| | Tidal Volume* | | | |

| Phagocytic | Inflammatory | Anti-Inflammatory | User Specified** | User Specified** |
|---|---|---|---|---|
| PMN #'s | [TNF-α]*** | [IL-10]*** | | |
| Monocyte # | [IL-1]*** | [IL-4]*** | | |
| PMN Apoptosis*** | [IL-6]*** | | | |

*Airway impedance and pulmonary compliance are measurable in mechanically ventilated patients by using a Proportional Assist Ventilator
**The User Specified areas indicate the capacity to enter and organize any additional parameters
***Parameters where new technology would aid in safe, readily repeatable measurement (for example, with very small blood volumes, in a regular, automated fashion)
[ ] Denotes "concentration of"

Patient parameters that may be used to evaluate the integrity of the cardiovascular system include any parameter that can be accurately measured at regular intervals (either from absolute measurements or from a waveform) that reflects the function of the heart and blood vessels. There are numerous potential variables amenable to variability analysis over time within the cardiovascular system. This includes heart rate, the first patient parameter that has undergone extensive evaluation of its variability. The interval between heartbeats may be measured precisely by an electrocardiogram, and is known as the R—R' interval. Other parameters that are part of the cardiovascular system and are subject to real-time accurate measurement include blood pressure, cardiac output, central venous pressure, systemic vascular resistance, and others. Blood pressure may be measured with standard arterial indwelling catheters or with an automated brachial artery sphygmomanometer. Cardiac output may be continuously measured with transesophageal echocardiography or chest impedance measurement. Central venous pressure may be measured by a catheter placed within the proximal superior vena cava. Other devices may prove to be more reliable or accurate. Important to the selection of monitoring devices will be the lack of artefacts, ease of rapid measurement, and patient safety. Nonetheless, any parameter subjected to continuous, accurate measurement, if only for brief periods, can provide data for variability analysis and display over time.

Parameters representing the integrity of the respiratory system include those indicating adequate oxygenation of the blood and tissue, appropriate ventilation, arterial pH, respiratory rate and respiratory mechanics. The more accurate the measurements of the parameters, the more useful variability analysis over time becomes.

A situation in which a patient is on a mechanical ventilator deserves special mention. Most current ventilators deliver the same pressure or volume to the patient from breath-to-breath. This limits, but does not completely abrogate the normal variability that is a component of a normal respiratory function. For example, if a patient is on pressure support, despite having the same pressure present to support their ventilation, there is slight variation in the tidal volume from breath to breath. Similarly, pressures may change slightly on volume control ventilation. It may therefore be possible to extract information on respiratory variability using such ventilators. However, other ventilators exist which provide dynamic alteration of both pressure and volume, which improves the significance of the respiratory variability. Specifically, a proportional assist ventilator permits the breath-to-breath alteration and measurement of multiple respiratory parameters, including airway resistance, pulmonary compliance, tidal volume, peak airway pressure. Therefore, one use for the proportional assist ventilator is where useful data to evaluate respiratory variability is provided.

Numerous other parameters, as shown in Table 1 (above), may be measured and the resulting data stored for a subsequent variability analysis. It is important to note that the patient parameters described do not form an exclusive list of patient parameters that can be analyzed using the variability analysis server 24. Rather, the variability analysis server 24 can accommodate any number of patient parameters that are subject to real-time, accurate measurement. Thus, when technology becomes available to measure other patient parameters, related data may be input along with the variables described, in order to provide an even more complete analysis of physiologic or pathologic variability.

In the variability analysis server 24, a variability time series is created for each patient physiological parameter. First, the user can set the interval and step for data monitoring over a period of time. That is, the variability analysis is performed on an interval and moves stepwise through the data in time. Collecting the data involves retrieving or accepting measured data points acquired by patient interfaces 28, for example, and storing the data points for subsequent analysis. The data collecting step also includes monitoring a quantity of data collected. For example, initial analysis may begin after approximately 1000 data points (for example 15 minutes of heart rate measurement) have been collected. For each patient parameter $v_k$, a user, typically an attending physician, may select the number of data points $m_k$ to collect in order to perform the variability analysis. Recommended settings may be provided by the central service 10 as well.

The method computes the time period represented by the selected number of data points. Thereafter, all subsequent calculations are based on the period of time required to collect the $m_k$ data points. Data updates preferably occur as frequently as possible, preferably occurring each interval. An interval is defined as the time required to perform the variability analysis for an individual patient parameter. Following the iteration of the next steps, the variability is re-evaluated based on data collected since the last analysis was performed (i.e. next step). For example, if an interval is approximately 1 minute, about 100 data points of heart rate data are collected in each interval. The collected data displaces the oldest 100 data points previously stored, permitting a new variability analysis to be performed based upon the latest $m_k$ data points. This process enables dynamic evolution of the analysis. In order to correlate data to a particular time period, time stamps are associated with the data, as discussed above.

Figure 5:
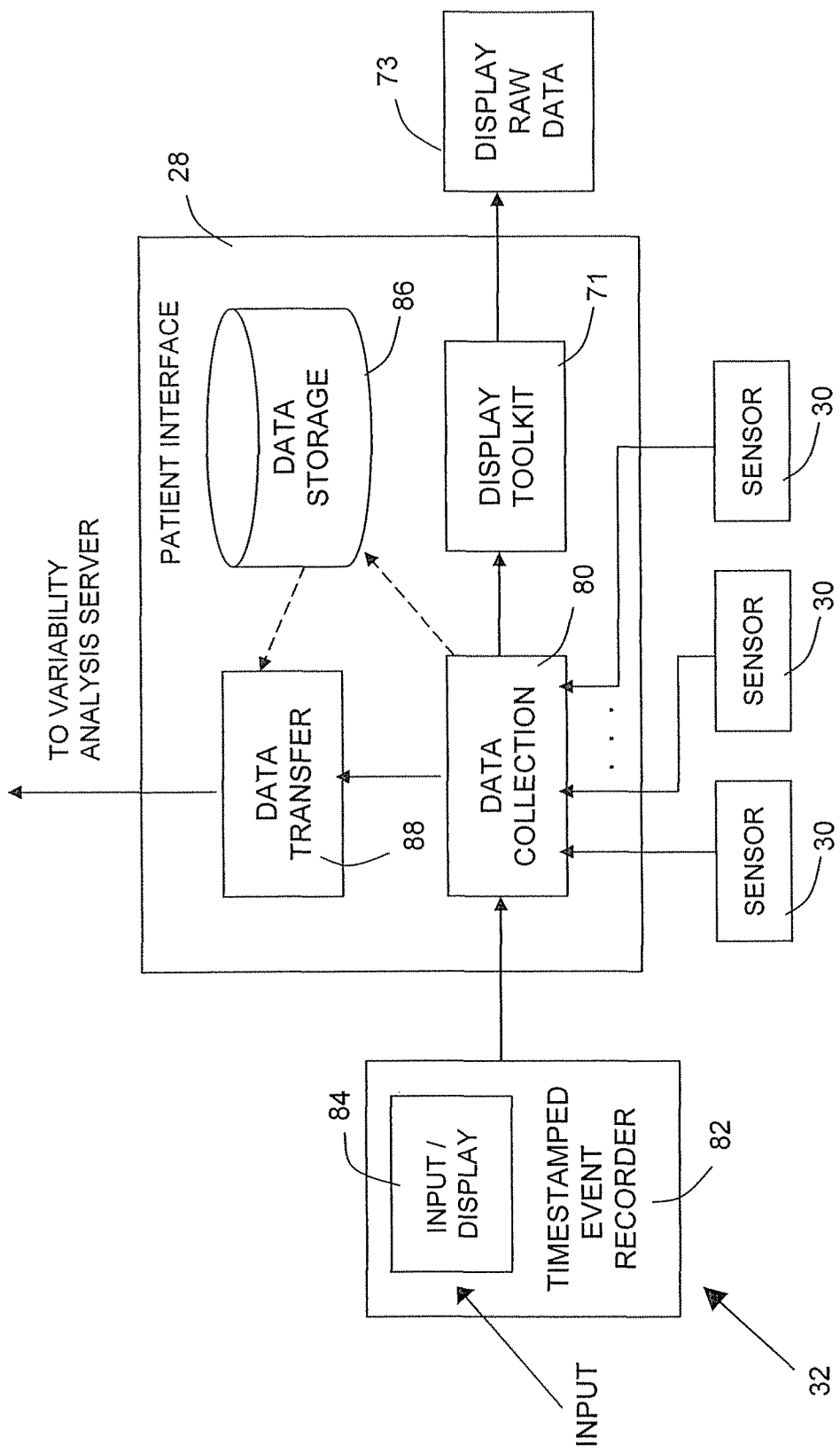
FIG. 5 is a schematic block diagram of the patient interfaces shown in FIGS. 2 to 4.
Figure 24:
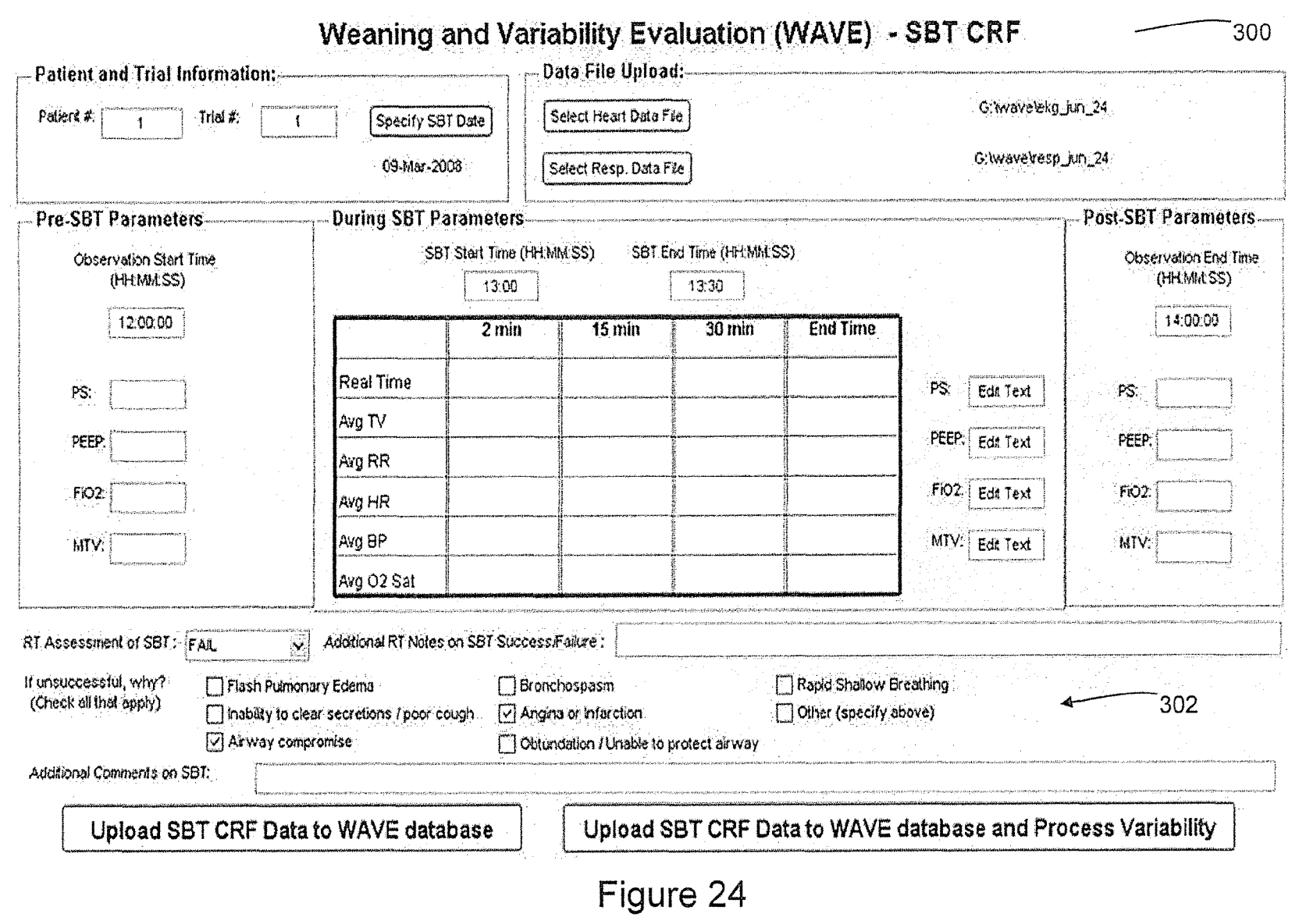

Turning now to FIG. 5, the patient interface 28, modified to be used within the system 12, is shown in greater detail. The sensors 30, which gather data from the patients 26 (or user 26) feed or otherwise make available the acquired data to a data collection module 80 in the patient interface 28. The data collection module 80 can be embodied in software, hardware or both, and also receives the time stamped event data 32. Between the sensors 30 and the data collection module 80, it will be appreciated that analog-to-digital (A/D) conversion is typically performed to convert the analog sensor data to digital data for subsequent processing. In this embodiment, the time stamped events 32 are captured through a time stamped event recorder 82. The time stamped event recorder 82 provides an interface for, e.g. the health care worker 34 to record the clinical events, which associates a particular event with a particular time. This can then be associated with the data acquired from the sensors 30 at that time. The recorder 82 preferably provides both an input mechanism and display 84, which can be separate components or can both be provided through a single mechanism such as a touchscreen. FIG. 24 is an example interface 300 that illustrates one way in which to obtain clinical events 32 for the time stamped event recorder 82. It can be seen that several selection boxes 302 can be provided to enable clinical event data to be recorded before the data is uploaded to the variability analysis server 24. The ability to "upload" waveform data and clinical data simultaneously enables, among other things, the following: comparison of clinical data and variability data, provision of a "report" encompassing both clinical and variability data, and performance of standardized multi-center research trials where variability is compared to standard clinical criteria. It will be appreciated that the recorder 82 can also be configured to receive audio or video inputs and can also be configured to automatically observe and record events, such as those that are triggered by another machine or even through automated visual processing.

Some or all of the data that is collected by the data collection module 80 can be used with a display toolkit 71 to display the raw data for the user/patient on a display 73. The data can also be stored locally in a data storage device 86, or can be transferred directly through a data transfer module 88. The data transfer module 88 represents the software and/or hardware that is used to provide connectivity between the patient interface 28 and the server 24 and thus typically includes a transmitter configured for either wired or wireless transmission. The data transfer module 88 can also be used to perform steps of data compression/decompression or file conversion as needed.

Figure 6:
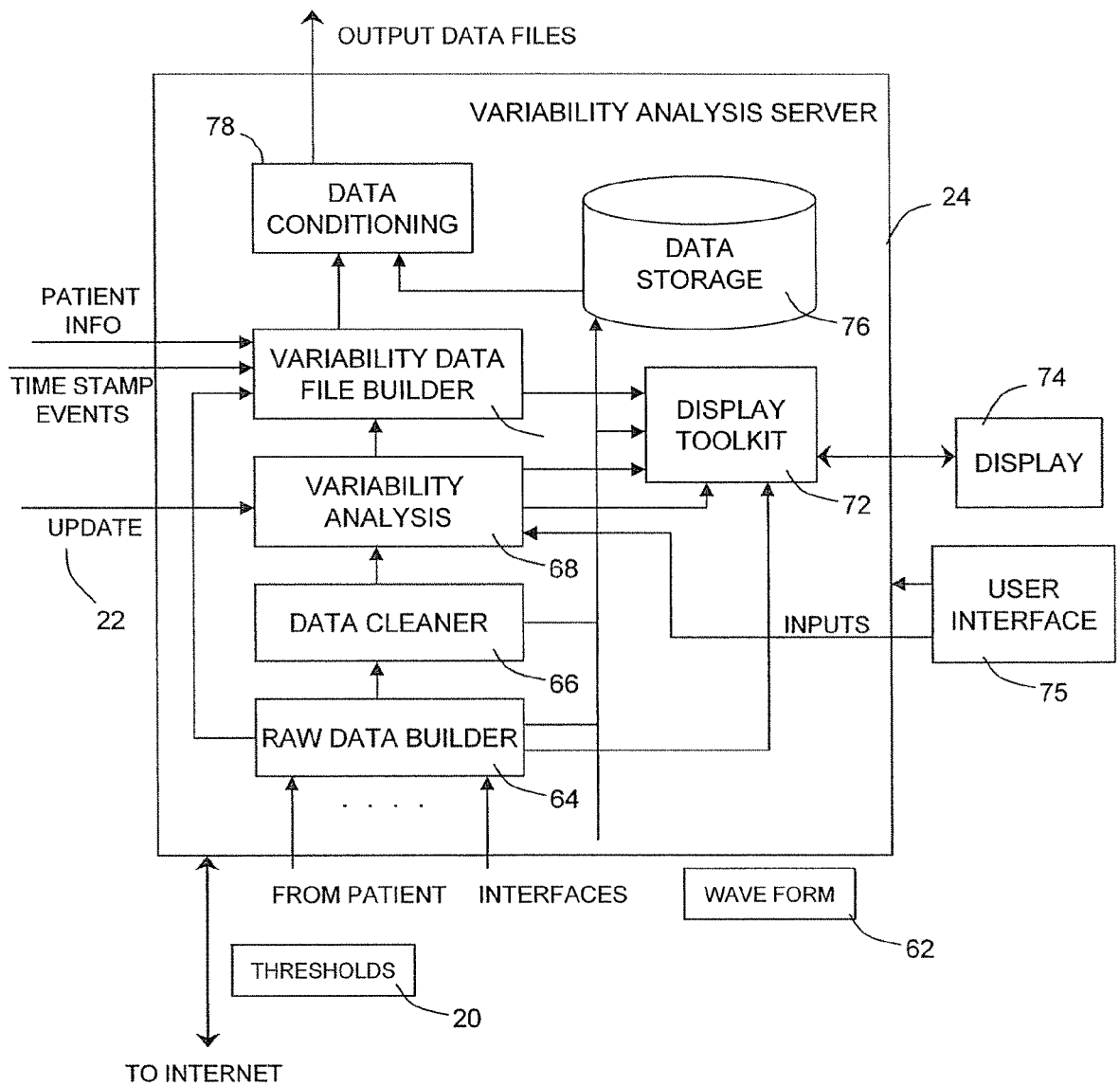
FIG. 6 is a schematic block diagram of the variability analysis servers shown in FIGS. 2 to 4.

In general, as shown in U.S. Pat. No. 7,038,595 to Seely, the data collected by patient interfaces is stored, and then such data is then available to a process for performing an individual patient variability analysis, the output of which can be displayed. In some embodiments, the apparatus can be centralized, e.g. at a nurse's station in an ICU. The individual patient interfaces communicate data to a central processor for multiple patient data collection. The collected data is then stored and is available to be processed by a multiple patient variability analysis routine, the output of which can be displayed. A user interface can be provided with the apparatus, to permit a user to format and control the multiple patient variability display. This, e.g., enables a nurse at a nurse's station to monitor multiple patients in a ward, such as an ICU. In another embodiment, both individual and patient and multiple patient configurations can be used. Turning now to FIG. 6, further detail concerning the variability analysis server 24, which is configured to operate within the system 12, is shown.

Figure 25:
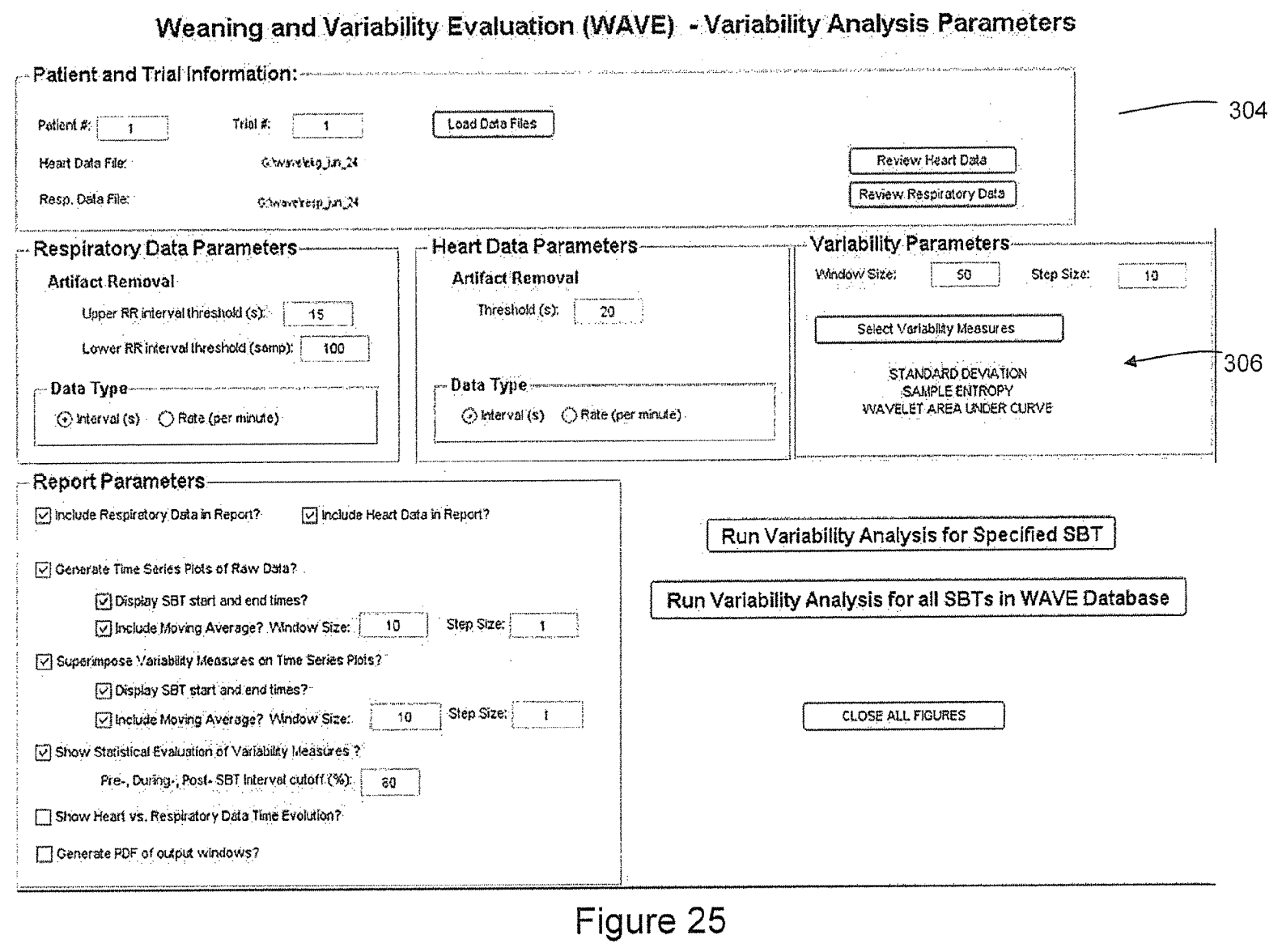

As can be seen in FIG. 6, the data collected by the patient interfaces 28 is transmitted to the server 24 and input to a raw data builder 64. The raw data builder 64 extracts raw data from the waveform 62 produced by the respective sensor 30. The raw data builder 64 can extract the time-series from the waveform that then undergoes variability analysis; e.g., the inter-beat interval time series is extracted from the electrocardiogram, the inter-breath interval extracted from the capnograph, and so on. The waveforms 62 are also preferably stored in a data file storage device 76 for later use in building the data packages 18 and can be used by a display toolkit 72 to output the waveform 62 on a display 74. The server 24 also preferably includes a user interface 75 for interacting therewith. For example, as shown in FIG. 25, an GUI 304 can be provided using the interface 75 for configuring the variability analysis type 306 and other parameters. It will be appreciated that the GUI 304 can be customized for specific trials or studies or can provide a generic interface. The output from the raw data builder 64 is fed to a variability data file builder 70, which creates the data packages 18 and appends any other files or related data thereto. This output is also fed to the display toolkit 72, which can output the raw data on the display 74, and is also fed to a data cleaner 66. The data cleaner 66 identifies and removes artefacts and other noise from the raw data such that it is suitable for use by a variability analysis module 68.

It may be noted that there are many techniques that can be used to quantify artefacts at each interval in the data, e.g. a Pointcaré Plot. Also, different variability analysis techniques (e.g. wavelet, frequency domain etc.) have different thresholds for how much artefact can be handled without compromising the variability analysis. For example, the data cleaner 66 first determines how much artefact is present and then determines which technique(s) can handle that amount of artefact. For example, a particular set of data may have too much artefact for performing a fast Fourier transform, but could be handled by a wavelet analysis. More discussion of these techniques is provided later.

The variability analysis module 68 performs the variability analysis and receives and processes the update data 22 and any other inputs necessary to perform the variability analysis. As can also be seen, the threshold data 20 is obtained by the variability analysis server 24 and used as appropriate. The variability analysis module 68 may output variability data (i.e. separate from the data packages 18) if desired, which can be used by the display toolkit 72 to output on the display 74. The variability data file builder 70 also receives the results of the variability analysis as an input for building the variability portion(s) of the data packages 18, and receives additional patient information 48 if applicable. Prior to transmitting the data packages 18 to the central service 10, a data conditioning stage 78 is used to filter, amplify, compress and otherwise prepare the data for transmission. It can be seen in FIG. 6 that at any stage, the output data is preferably stored in the data storage device 76 such that it may be accessed, processed and viewed at a later time or during the variability analysis.

It may be noted that the variability analysis module 68 can be configured for and programmed to perform any type of variability analysis. Similarly, the data cleaner 66 can be programmed to perforin any desirable data cleaning or conditioning. The following provides more detail on how the data cleaning and variability analysis may be performed.

The first step in variability analysis is typically to select data points. This can be done at the data cleaning stage 66 or upon execution of the variability analysis module 68. Real data measurement systems often acquire spurious signals that are not relevant to the required analysis. As discussed above, these spurious data points are referred to as artefacts, and it is desirable to remove them in order to make analysis more meaningful. There are many acceptable methods for finding and removing artefacts from sequences of data collected from a wide variety of medical devices. A plurality of methods may be used. As also noted above, one technique is to use a Pointcaré plot. A Pointcaré plot represents differences between consecutive data points. The absolute value of a difference between a data point and the preceding data point ($X_i$-$X_{i-1}$) is plotted on the x-axis, and the absolute value of a difference between the same data point and the subsequent data point |$X_i$-$X_{1+1}$| is plotted on the y-axis. A visual evaluation may be used to eliminate artefact data.

A current data point, and the previous data points may be collected and displayed on the same graph, giving the appearance of a cloud. A user can draw a gate around the data points using tools available through the user interface 75, and a pointing device, for example, thus excluding widely divergent, artefactual data points. The benefit of the Pointcaré plot is that there is a dynamic display of the data in evolution, and there is the ability to dynamically alter the gate. In addition, if too high a percentage of data falls outside the gate, an alarm signal is preferably activated.

Again, other methods may also be used to remove artefactual data. An absolute value of a parameter may be plotted in succession on a time scale evolution plot, permitting rapid inspection of the data, and removal of artefacts. The original measurement, whether it is an R—R' interval for heart rate, a blood pressure tracing, etc., is available to permit the data cleaner 66, or a user to determine whether individual points should be discarded or added. Thus, storage of data is useful not only for analyzing the data but also reviewing and analyzing previously recorded data. Data artefacts can thus be removed by inspection of the original data measurements.

Several methods may be used to select the data. Different methods may be applied to different data sets, with distinct data collection techniques. Therefore a user can select the method by which data artefacts are removed using tools available through the user interface 75. Certain methods of selecting the data are ideal for specific types of data measurement. For example, a Pointcaré Plot has been found to be suitable for heart rate analysis.

It may be noted that in some cases, some of the variability measures (to be exemplified below) can be unreliable in the face of significant non-stationarity. Therefore, it is beneficial to monitor non-stationarity in addition to variability in order to correct any defects.

The second step in variability analysis is computing all variability parameters for each of the respective patient parameters. The variability represents a measure of a degree and character to which a particular patient parameter fluctuates over time. There are many methods for performing variability analysis. There is no consensus within the scientific literature that a single method of variability analysis is superior for all patient parameters. Heart rate variability (HRV) has been the most extensively studied, and despite considerable research, no method for determining variability has proved consistently better than others. In fact, numerous authors have demonstrated the clinical utility of evaluating HRV using different methods. Different patient parameters may require different methods for evaluating variability, due to differences such as altered statistical properties of the frequency distributions of the respective patient parameters.

In one embodiment, the variability analysis server 24 is adapted to display several options for variability analysis to the user on the display 74, and to advise the user through user interface 75 and/or display 74, respecting a suggested method for a particular patient parameter, based upon an algorithm for evaluating the data sets.

Currently, the simplest method for computing variability parameters involves the calculation of mean and standard deviation of the frequency distribution of a selected data set. This information can be updated over time (e.g. continuously) and displayed visually as a graph. Statistical interpretation of the frequency distribution is dependent upon whether the distribution is normal or lognatinal. There are standardized means of evaluating whether a distribution is accurately represented by a normal or log-normal curve, which include evaluation of kurtosis and skew. By calculating the kurtosis and skew, the user may be directed towards choosing an appropriate distribution. By evaluating the frequency distribution, the mean and standard deviation would represent the variability parameters for the particular patient parameter under evaluation.

In addition to the mean and standard deviation of the frequency distribution, numerous other methods for computing variability parameters exist. Methods for evaluating variability include spectral and non-spectral analysis, time-frequency analysis (wavelet analysis), calculation of Lyapunov exponents, approximate entropy, and others (Seely and Macldem, 2004—cited above). Preferably the user is presented through the user interface 75 with a choice of several methods, and assisted in selecting a particular method. The results of the variability analysis yield a variability parameter for each patient parameter under evaluation. The variability parameter may then be displayed, and updated over time. In each cycle, the updated variability is displayed.

Figure 9:
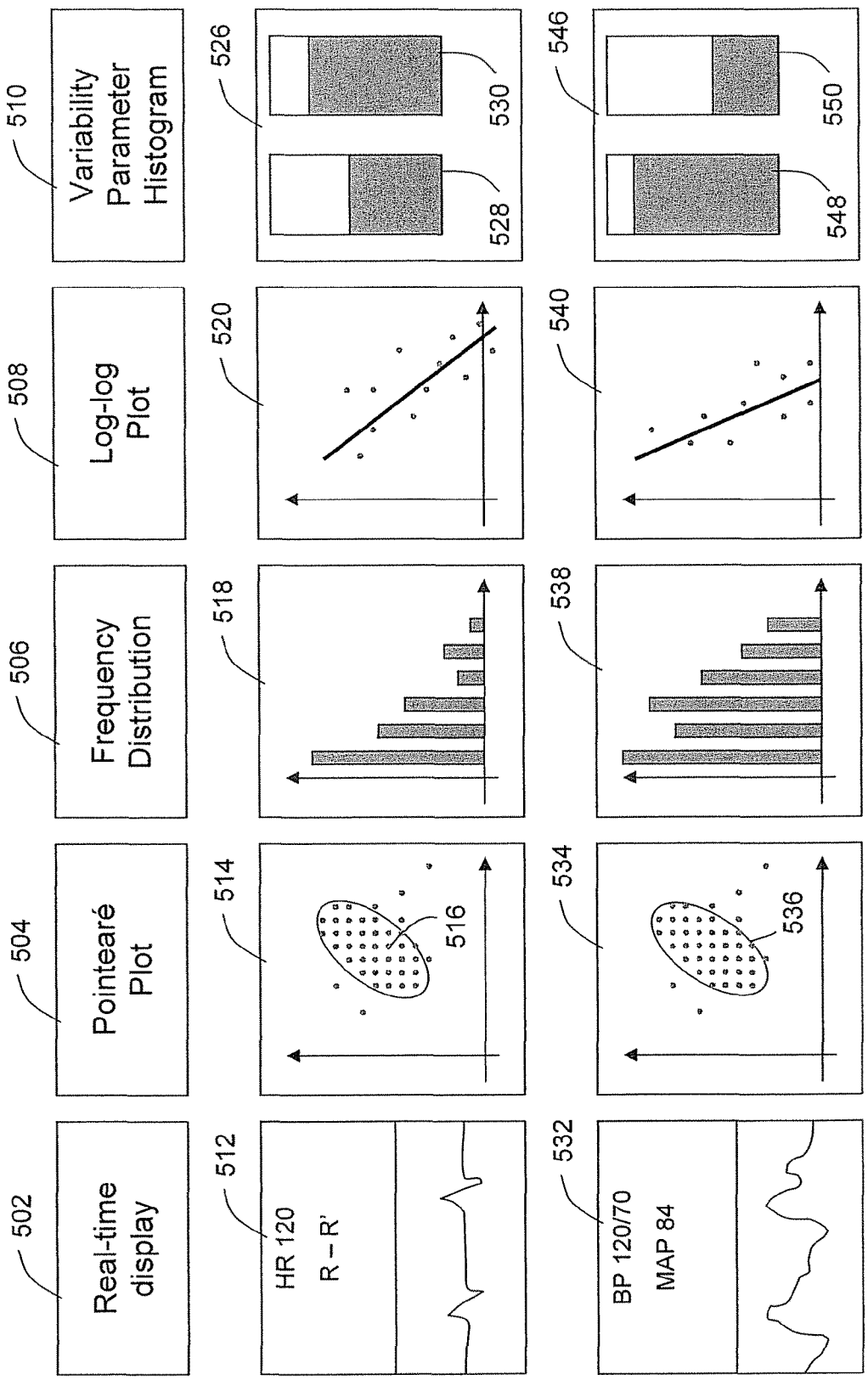
FIG. 9 is a block diagram illustrating exemplary displays for individual variables.

As shown in FIG. 9, the variability analysis process preferably begins with a real-time display 512, 532 of the respective patient parameters, heart rate 512 and blood pressure 532 in one example. A Pointcaré plot 514, 534 is used, for example, to eliminate data artefacts by establishing a gate 516, 536. A frequency distribution histogram 518, 538 is calculated using the squared difference from the mean of the Pointcaré plot. This method is suitable for data sets that demonstrate 1/f noise. It is a tool for generating a frequency distribution of dispersion from the mean, where all values are positive. The data is plotted in frequency bins, where each bin represents a proportional amount of variation, as measured by the squared difference from the mean. The bins are represented as a histogram, with the frequency on the y-axis, and increasing variation on the x-axis. The bins on the left are normally most full because they represent very common, small variations. The bins on the right, with increasing x-axis, represent large frequency variations, and are usually smaller. In every cycle, the histogram is updated. The Log-log Plot 520, 540 is simply a linear representation of the frequency distribution histogram 518, 538 on a log-log plot of frequency vs. variation. The straight-line distribution of points is characteristic of 1/f noise. The best fit of a straight line through the data points may be derived using standard linear regression analysis, and can also help inform the user respecting the appropriateness of this particular technique. The variability analysis module 68 calculates the slope of the line 522, 542 of the log-log plot and the x-intercept 524, 544. These values can be displayed as pairs of dynamic variability parameter histograms 526, 546. The slope is represented by one histogram 528, 548 and the intercept by another histogram 530, 550.

In general, the display of variability involves a way by which a user is able to access the variability of patient parameters computed by the variability analysis method selected by the user. One way for displaying variability parameters is dynamic variability histograms 526, 546 (FIG. 9) which are represented as columns that increase or decrease in height based on changes in the variability of patient parameters over time.

"Normal" ranges for the variability of each patient parameter for each patient can be determined by analysis over time. Continued research will also provide guidance in this area. Alarms can be set so that if a variability histogram is within the normal range, it is displayed in one color (green, for example). If the value of the histogram rises above or falls below the normal range, it is displayed in a different color (red, for example). The histograms 526, 546 are updated at every cycle.

Figure 10B:
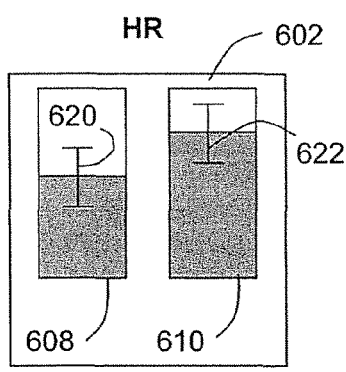
FIG. 10B illustrates exemplary plots correlating variability histogram data points for the variability histograms of FIG. 10A.
Figure 10B:
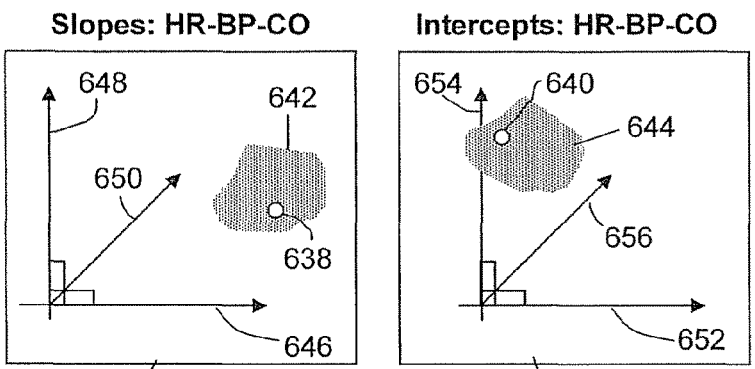
Figure 10B:
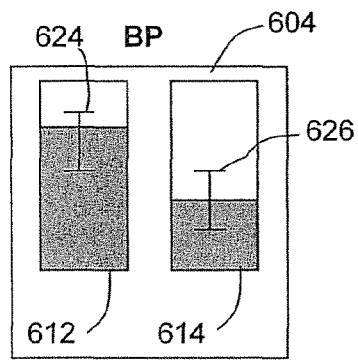
Figure 10B:
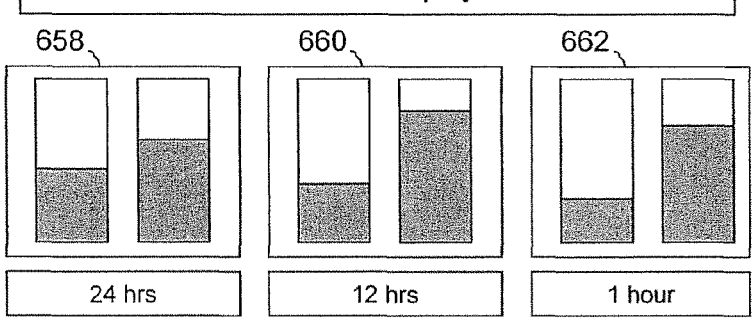
Figure 10A:
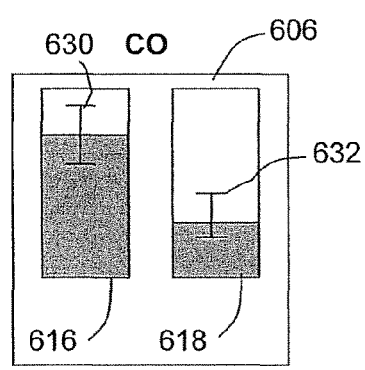
FIG. 10A illustrates exemplary variability histograms.
Figure 10A:
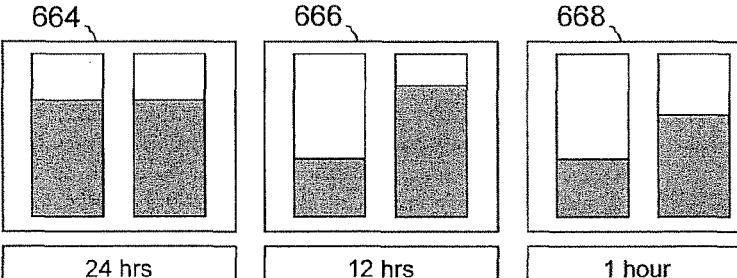

FIG. 10A illustrates exemplary variability histograms similar to those shown in FIG. 9. Examples are illustrated for heart rate 602, blood pressure 604 and cardiac output 606. Another useful value that can be displayed is a standard deviation of the most recently selected period of variability analysis. This can be super-imposed on the variability histograms as an "I" bar 620, 622, 624, 626, 630, 632.

As described above, the clinical therapeutic potential of variability analyses of multiple parameters over time is the ability to distinguish pathologic from physiologic systemic properties by monitoring patterns of alterations M. the variability of multiple patient parameters. Thus a display can be tailored to best represent the current state of any individual patient with a view to evaluating the physiologic and pathologic properties of individual organ systems, by following the variability of parameters intrinsic to that system.

It may be recognized that different organ systems are interrelated and mutually dependent. However, it is beneficial to distinguish between organ systems, because therapeutic intervention is commonly directed towards individual organs. Examples of organ systems include the cardiovascular system, respiratory system, the hematologic system, central nervous system, liver and metabolic system, kidney and waste excretion system.

Thus, flexibility in the display of variability of multiple parameters should be provided. The user may select various display options to profile an organ system or a combination of interdependent organ systems. In addition, the user may select any one of: an individual patient display adapted to display the variability of all monitored parameters for an individual patient; an individual patient organ specific display, which can display a selected organ system for an individual patient; a multiple patient display, which can simultaneously display the variability of patient parameters for all patients in a monitored ICU; and a user specified variability display, which can display the variability of user selected patient parameters.

The ability to review changes in variability of patient parameters over time increases the clinical utility of the variability analyses performed using these techniques. FIG. 10B illustrates a Variability Review display 634, 636, which is a visual representation of three selected variability parameters 602, 604, 606. One graph 634, represents slope values of the selected parameters 608, 612, 616. The other graph 636, represents the intercept values of the selected parameters 610, 614, 618. In the examples shown in FIG. 10B, for each graph, the heart rate values are plotted on the x-axes 646, 652; blood pressure values are plotted on the y-axes 648, 654; cardiac output values are plotted on the z-axes (depth) 650, 656. Alternatively, the z-axis (depth) can be represented by shades of color. The current variability values are preferably represented by a large dot 638, 640 and the most recent calculated variability values over a set period of time are represented by small dots 642, 644. This permits a visual representation of the data, to enable the user to observe movement of the "cloud of data" over time, as well as any correlation between the selected parameters.

Continued research and user observation helps define desirable physiological patterns of variability. Specific movement of the cloud of data may be desirable and may be stimulated using therapeutic interventions. Thus, a variability review display can be used to facilitate positive intervention.

In addition to the patient and organ specific displays, a display of variability may also be organized into three principal modes: Instantaneous Display, Review Display or Combined Display.

The Instantaneous Display mode provides real-time display of current variability parameters, the process by which data selection has taken place, and the graphs related to the particular method of variability analysis used for an individual patient parameter. This mode may be used in any of the four user-selected displays (Individual Patient Display, Individual Patient Organ Specific Display, Multiple Patient Display and User Specified Variability Display).

The Review Display (FIG. 10C) permits the user to identify the patterns of alteration in variability parameters over a selected period of time, for selected individual or multiple patient parameters. The Review Display provides the user with a time-compressed, animated display of the variability of selected patient parameters during any selected time period for which data exists. This display mode is similar to a video of the variability over time. This display permits the user to determine the progression of the variability of patient parameters of an individual patient. It also permits the user to determine a response to an intervention, a general progression of illness, or a need for further intervention. Averages of variability in patient parameters, calculated for specific time periods (for example, four hours prior to and four hours following an intervention) can be included in a Review Display.

The Combined Display mode provides a combination of real-time display of current patient parameters, as well as a display of a previous (specified) period of time.

Figure 10C:
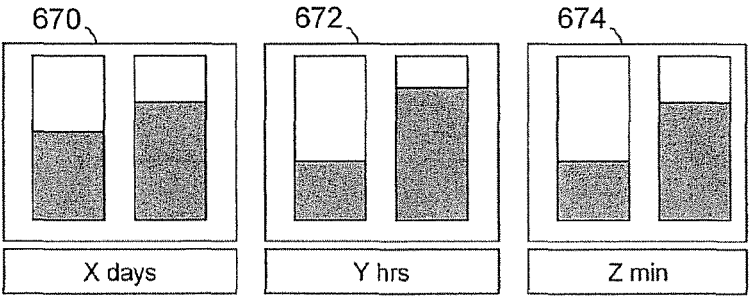
FIG. 10C illustrates exemplary review displays of variability histograms.

FIG. 10C shows three examples of review display. The first row of FIG. 10C shows an example of combined display in which the variability of a patient parameter 24 hours ago (658) is displayed beside the variability of 1 hour ago (660), and the variability in real-time (662).

The second row of FIG. 10C illustrates a review display in which a variability progression is displayed for a patient parameter showing a progression of variability from 48 hours (664), 24 hours (666) and 1 hour (668).

The last row of FIG. 10C shows another review display in which the variability of the patient parameter is displayed at X days (670), Y hours (672) and Z minutes (674).

As will be explained in greater detail below, the display toolkit 72 enables the user to extend from the above general display features into a more sophisticated and convenient user interface (UI). The extended display capabilities can be realized, in part, due to the organization of the acquired variability and waveform data.

Figure 26:
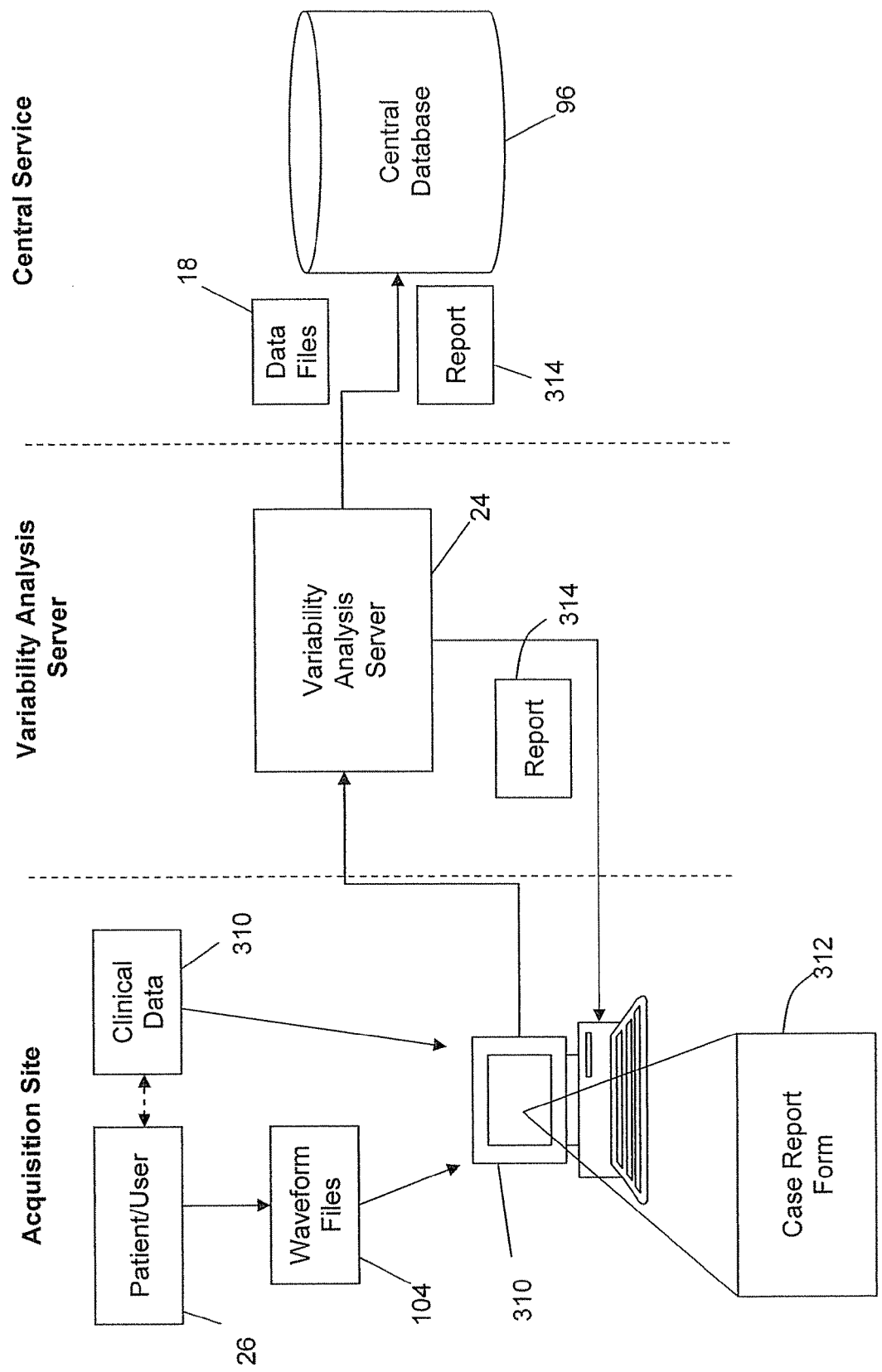
FIG. 26 is a schematic block diagram showing a process for retrospectively analysing waveform data using the variability analysis server.

It may be noted that although the above examples illustrate the real-time analysis of variability over time through a direct interface between the patient interfaces 28 and the variability analysis server 24, as shown in FIG. 26, various other configurations are possible. Turning now to FIG. 26, it can be seen that waveform data obtained from a patient or user 26 can be acquired and stored as waveform data files 104 at any time and associated with clinical data 310 for that user 26. The clinical data 310 can represent any data pertaining to the user, the nature of their disease, demographics, clinical events, etc.

The waveform data files 104 and clinical data 310 can then be used at some other time to perform a retrospective analysis. In this example, a Case Report Form 312 user interface can be provided at a workstation 310, which enables the data to be uploaded to the variability analysis server 24. It may be noted that the variability analysis server 24 can be local or remote and thus the acquisition site can represent any location or entity that is capable of receiving and/or storing and/or processing the data to be uploaded. The variability analysis server 24 may then process the data retrospectively according to the principles exemplified above and a report 314 generated pertaining to the variability analysis of the data that was uploaded. It will be appreciated that, as shown in FIG. 26, the reports 314 can also be sent to or downloaded by the central service 10 and stored in a central database 96 (see also FIG. 12). Similarly, the data packages 18 comprising the data files, detail of which is provided below, can also be provided to the central service 10 by the variability analysis server 24. It can therefore be seen that the acquisition of patient data, subsequent variability analysis and storage, processing and reporting of results can be accomplished in any suitable physical configuration and the stages shown can be temporally spaced if appropriate.

Figure 7:
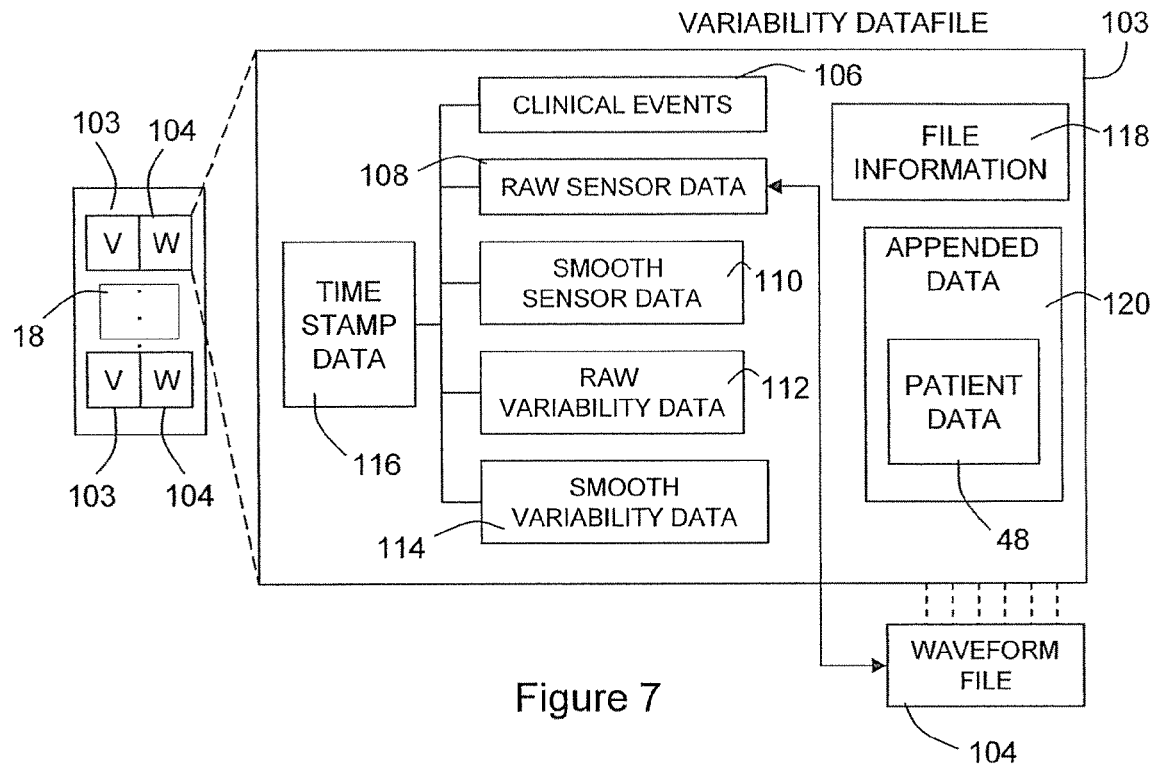
FIG. 7 is a schematic block diagram of the variability and waveform data files shown in FIGS. 1 to 6.

As noted above, the variability analysis server 24 processes the waveform data 62 sent from the patient interfaces 28 to ultimately create variability data files 103 for of the data packages 18, which can be sent to the central service 10. FIG. 7 illustrates a general data structure for the data packages 18. As discussed above, each data package 18 may comprise a variability data file 103 and a corresponding waveform data file 104 for each organ, parameter or variable. The variability data file 103 includes several sets of data for each parameter, each associated with a common time scale. As shown in FIG. 7, the variability data file 103 includes a set of clinical events 106 that are obtained from the time stamped event data 32, e.g. as entered using the timestamp event recorder 82. The variability data file 103 also includes raw sensor data 108 extracted from the waveform 62, smooth sensor data 110 created from the raw sensor data 108, raw variability data 112 generated during the variability analysis stage 68, and smooth variability data 114 created from the raw variability data 112. These smoothed versions (110 and 114) are created from a roving average of the data in the raw versions (108 and 112) with a certain interval and step. It can be seen that all sets of data 106-114 are time-stamped with respect to each other through time stamp data 116. The time stamp data 116 is acquired along with the waveform and clinical events such that any data acquired by the sensors 30 is associated with a time stamp. In order to enable a user to view waveforms and other display outputs for multiple organ variability at the same time, a common time scale is used. The common time scale can be applied using any known technique such as curve fitting the data from separate parameters, and then selecting data corresponding to a point in time and finding the value on each curve.

The variability data file 103 is also associated with a corresponding waveform 62 by having associated with or appended thereto, a complementary or corresponding waveform file 104. The waveform file 104 also includes time stamp data 116 that enables the waveform 104 to be matched/aligned with the corresponding sets of data 106-114. The data packages 18 also includes a set of file information 118, which may be in the form of a header, footer, flag(s), etc. In general, the file information 118 is any information that pertains to the structure and properties of the data packages 18. As noted above, other data, typically associated with the patient being monitored, can also be appended to the data packages 18. As such, the data packages 18 optionally include a set of appended data 120 which may include the patient data 48 that was originally input to or obtained by the variability analysis server 24. In the example shown in FIG. 7, the file information 118 and appended data 120 is shown as being included in the variability data file 103 but it will be appreciated that such data 118, 120 can also be included in the waveform file 104 or as its own auxiliary or appended data file (not shown). It will also be appreciated that common file information 118 and appended data 120 can be associated with all variability data files 103 and waveform data files 104 in the data package 18. As such, it can be seen that any suitable data structure for organizing these data elements can be used and the one shown in FIG. 7 is purely illustrative.

Figure 11:
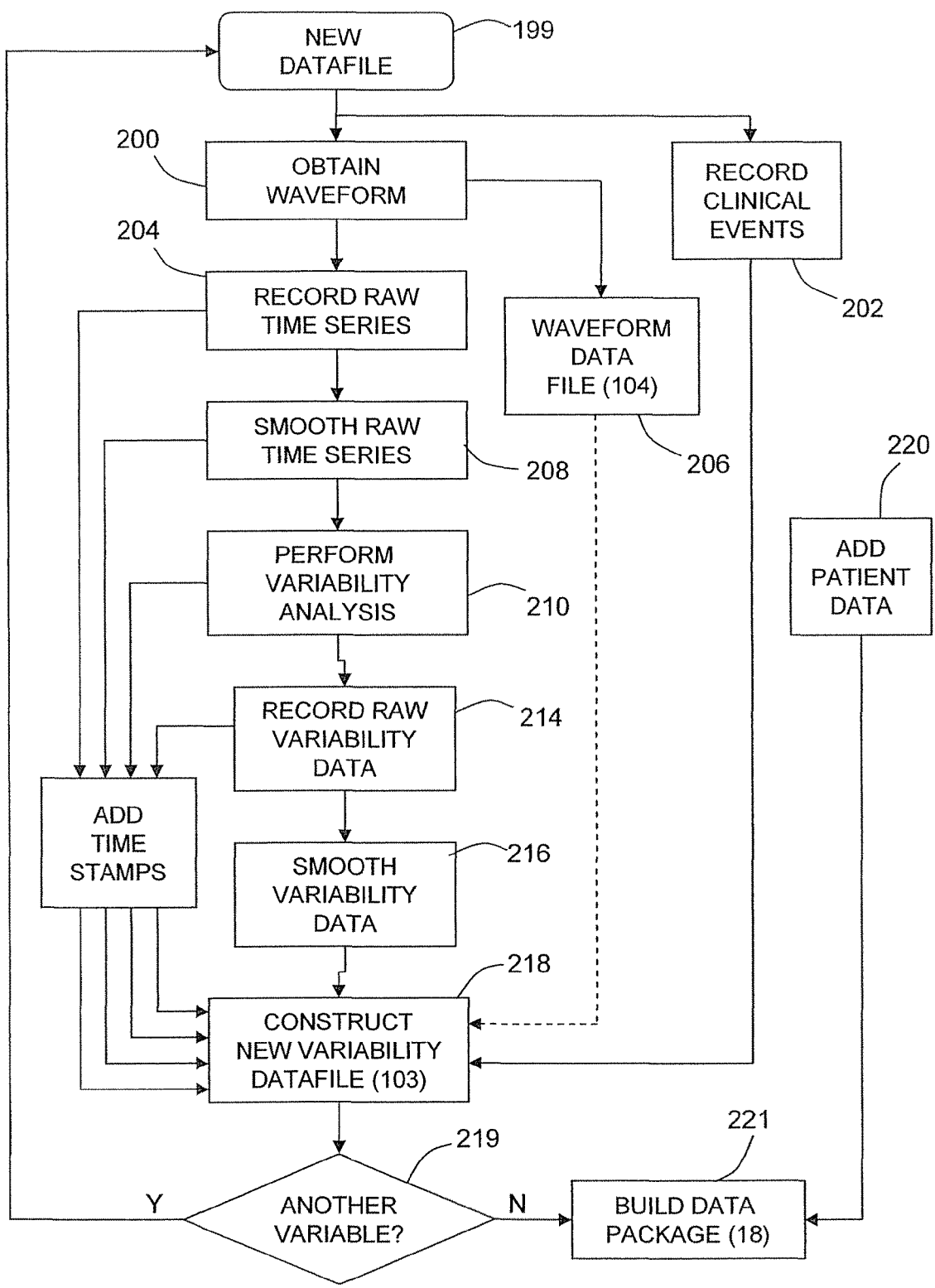
FIG. 11 is a flow diagram illustrating the construction of a data file as shown in FIG. 7.

FIG. 11 shows a flow diagram illustrating how the data packages 18 can be constructed. For each new data file routine 199 (i.e. for each parameter), at 200, the waveform 62 is obtained from the sensors 30, at 206, the waveform data file 104 is created and, if applicable, appended to a new variability data file 103 to create a new data package 18. While the waveform 62 is being acquired, the clinical events are recorded at 202, e.g. using the time stamped event recorder 82. As such, the clinical events data 106 is updated in the new variability data file 103 as events are recorded. At 204 the raw time series is recorded to produce the raw sensor data 108. The raw sensor data 108 is then used at 208 to create a smooth time series (i.e. a smoothed version of the raw sensor data 108) and added to the new variability data file 103 as the smooth sensor data 110. At 210, the variability analysis is performed on the data. At 214, the raw variability data 112 generated from the variability analysis at 210 is recorded and added to the new variability data file 103. This is performed using the appropriate variability analysis techniques yielding a plurality of variability time-stamped values. From this, the smooth variability data 114 is generated and stored in the new variability data file 103. It can be seen that at 218, all of the data sets created in the preceding stages are amalgamated, along with the appropriate time stamps to create the new variability data file 103. At the same time, the waveform data file 104 appended if applicable.

At 219, if another variable or parameter is being monitored, another new data file is generated for that parameter by repeating steps 200-218. Once all parameters have been analyzed, the data package 18 is generated by amalgamating all variability data files 103 and corresponding waveform data files 104. The patient data 220 and other file information 118 (not shown) may be added to each variability data file 103 or as a common set of identification data per data package 18.

Figure 8:
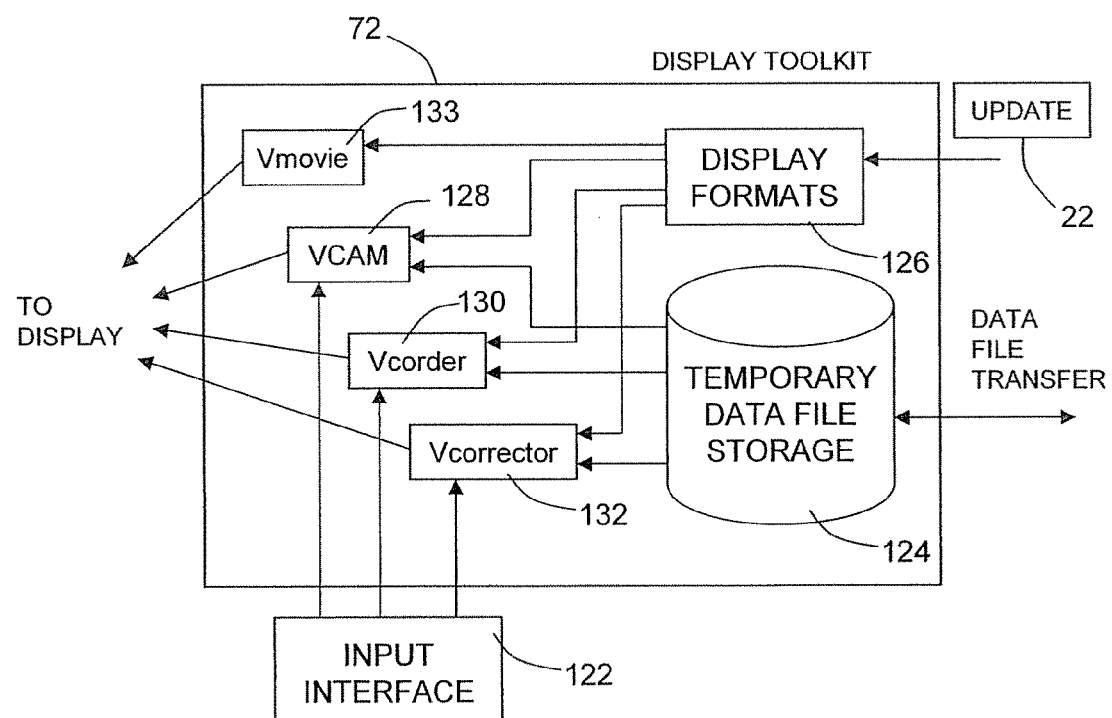
FIG. 8 is a schematic block diagram of the display toolkit shown in FIG. 5.

Turning now to FIG. 8, the display toolkit 72 is shown. It will be appreciated that the toolkit 71 in the patient interface 28 shown in FIG. 5 may include the same or similar components. The tools contained in the toolkit 72, as exemplified in the figures and explained below, represent examples of generic displays. The tools are designed to be maximally configurable and user friendly, namely so that one can change the length of the overall time series and the interval being considered for variability, as well as the step by which the interval moves forward in time. As such, the user can set the length of data and the interval and step as well as the type of variability analysis.

The toolkit 72 includes a temporary data file storage 124 for storing or caching data packages 18 that are to be displayed and analysed using the tools included in the toolkit 72. The toolkit 72 also includes a display format module 126 to enable the tools to handle the specific data format shown in FIG. 7 and to handle any updates 22 that are specific to how the data is processed for display purposes. The toolkit 72, in this example, includes a Vcam tool 128, which enables a user to magnify a variability data set in order to view the original raw data used to calculate the variability. This enables the user to also view different data sets (e.g. 106-114) together in order to compare, e.g. raw variability data with smooth variability data. Also included is a Vcorder tool 130, which enables the user to scan data packages 18 over time, e.g. by going forward and backwards with respect to time to show how variability has changed over such time. The Vcam tool 128 and Vcorder tool 130 may also be embedded in the same tool. The toolkit 72 also includes a Vcorrector tool 132, which is a display tool used to amend, annotate and otherwise change the data stored in a particular waveform data file 104 to improve the understanding and/or accuracy thereof. Also included is a Vmovie tool 133, which enables a set of data over time to be constructed and viewed in motion as a movie to provide a further way in which to view continuously changing variability at different intervals. As can also be seen, the toolkit 72 preferably interacts with an input interface to enable the user to interact with and use the tools included in the toolkit 72.

As noted above, the tools (and displays provided thereby) in the toolkit 72 represent examples of generic displays. The Vmovie tool 133 for example, represents a generic form of display, where any type of variability graph can be displayed along with the raw data above (see also FIG. 21 explained later), along with the interval of data that is being used for variability analysis, such that as the movie plays, the variability graph changes reflecting the interval noted above.

Figure 12:
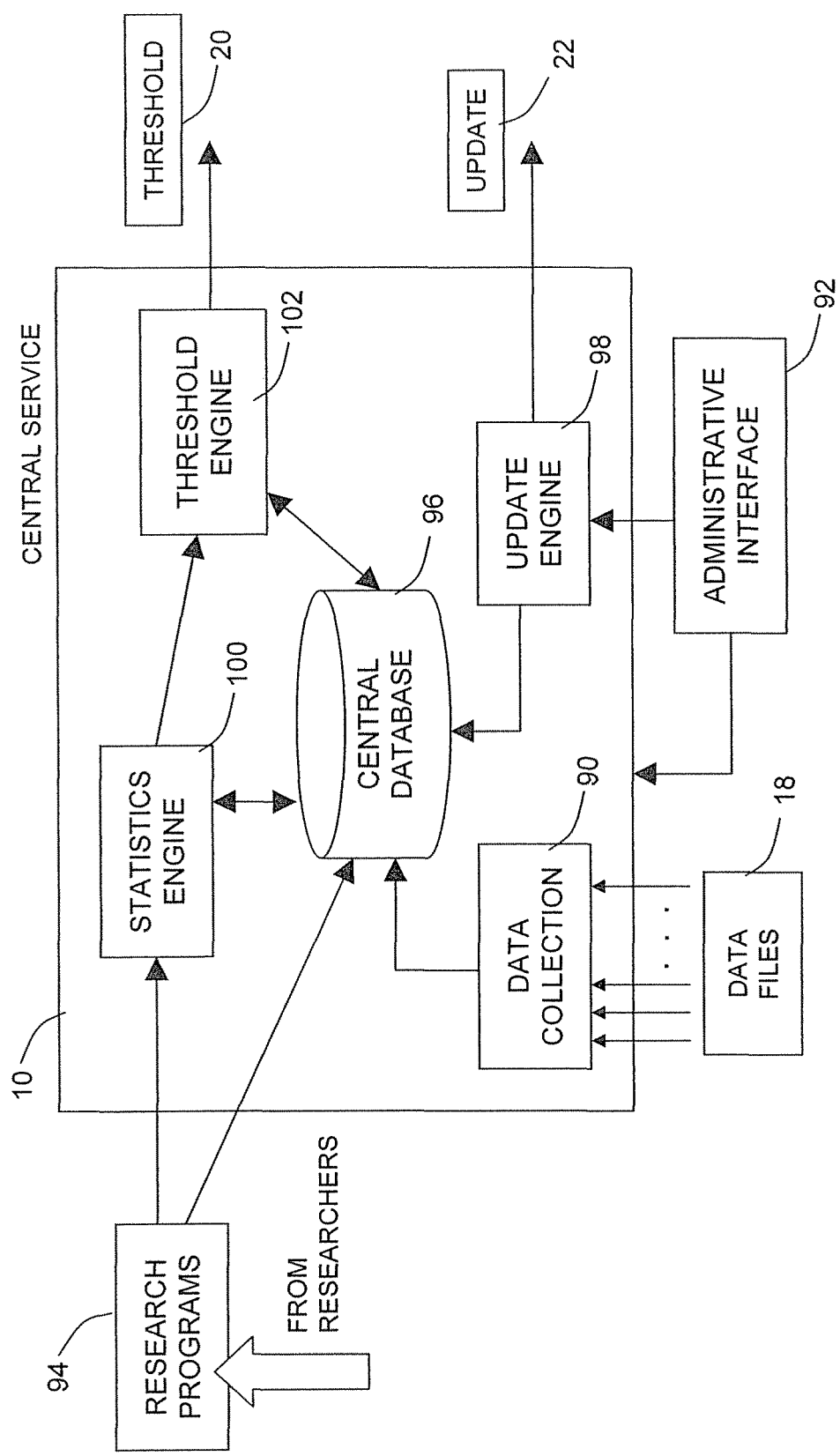
FIG. 12 is a schematic block diagram of the central service shown in FIG. 1.

Turning now to FIG. 12, further detail of the central service 10 is shown. The central service 10 includes a data collection module 90 for obtaining the data packages 18 sent over or downloaded from the Internet 14, which then stores the data packages 18 in a central database 96. The central database 96 generally represents any and all data storage performed by the central service 10 and should not be limited to any number of storage components, databases, formats etc. The central service 10 also preferably includes an administrative interface 92, either external as shown or internal, which enables administrative personnel to control operation of the central service 10. The data packages 18 stored in the central database 96 can be used by a statistics engine 100 for conducting evaluations of data from across various demographics or to target specific symptoms, trends, outliers, etc. The statistics engine 100 and the central database 96 may also interact with external research programs 94 that are under the control of researchers and that use the data stored in the central database 96 to conduct variability analyses across multiple patients. It may be noted that each data package 18 is specific to an individual and, as such, the central database 96 provides a tool for researchers to have access to data from many individuals over time to conduct more thorough and detailed analyses.

The central service 10 also includes a threshold engine 102 which is a software module or routine that uses input from the statistics engine 100 and the data stored in the central database 96 to generate a set of thresholds to enable the variability analysis servers 24 to conduct consistent analyses. The threshold engine 102 thus generates the threshold data 20 that can be sent over the Internet 14 to the various monitoring sites 16. Similarly, an update engine 98 is included, which is a software module or routine that takes input from the administrative interface 92 to generate system updates by way of update data 22. The update engine 98 generates update data 22 and distributes such data 22 over the Internet 14 to the various monitoring sites 16.

The update data 22 comprises any update to the software that performs variability analysis in the system 12. As explained above, each monitoring site 16 includes an analysis server 24 for performing the variability analyses. Given the connectivity provided by the system 12 shown in FIG. 1, the central service 10 can maintain up-to-date software throughout by preparing updates for each monitoring site 16 and distributing update data 22 to each variability analysis server 24. Since variability techniques are ever evolving and becoming more sophisticated, as new techniques and tools are developed, the server 24 can be updated remotely without requiring technicians to visit the monitoring sites 16 or to have the variability analysis servers 24 brought in to a service centre. Furthermore, the central service 10 can ensure that all monitoring sites are properly updated to maintain the effectiveness of the data gathering by requiring feedback or periodic polling etc. The central service 10 may also use the connectivity provided by the system 12 to charge a subscription service fee or per use/per update charge to create a stream of revenue. It can therefore be seen that the connectivity of the system 12 enables the update data 22 to re-synchronize and standardize software processes and formats throughout.

It should be noted that the update data 22 should also include the best interval and step as well as recommended variability techniques to be used for each clinical application and patient population. Therefore, the distributed system 12 can be leveraged to provide consistent information to each monitoring site 16.

The threshold data 20 represents generally the best threshold at which to issue an alert or to on a detected condition when performing a variability analysis. The threshold data 20 can be an evolving set of data that is based on a collaboration of the data acquired by gathering the data packages 18 and possibly through researcher, scientist and medical professional input. The threshold data 20 enables the central server 20 to continuously refine and update the operating and alert thresholds across the entire system 12 and also for specific clinic environments and different patient populations as discussed above.

Turning back to FIG. 8, the user interfaces for the tools included in the display toolkit 72 will now be explained in greater detail. The variability data generated using the variability analysis module 68 is conveniently amalgamated with the time series sensor data 108, 110 and the clinical events in the variability data file 103, which has associated therewith, a waveform data file 104. The variability data and waveform data can be output to the display 74 of the server 24 and the display toolkit 72 provides advanced features for analysing variability over time, using any suitable and available techniques.

For example, a range of variability analysis techniques can be used to assess heart rate (HR) and respiratory rate (RR) separately to provide individual measures of HR variability (HRV) and RR variability (RRV), as well as simultaneously to provide an overall measure of cardiopulmonary variability (CPV). Such techniques that are used, typically assess HRV, RRV, and CPV in real-time. The main techniques that will be used are as follows:

1) Time Domain: Standard deviation and coefficient of variation statistics are computed to evaluate signal variability. Time domain measures also involve computation of probability distribution curves (frequency histograms) which will result in statistics like kurtosis and skewness for assessing variability.

2) Frequency Domain Techniques: The analysis of the spectral frequency content of H R and R R signals are undertaken by utilizing the fast Fourier transform (FFT).

3) Time-frequency Domain: With the help of wavelet analysis signals can be analyzed in both time and frequency domain simultaneously to overcome issues such as non-stationarity and noise.

4) Complexity Domain: The amount of entropy or complexity or information in the analyzed signals can be assessed using the sample entropy (SampEn) and multiscale entropy (MSE) measures.

5) Scale-invariant Fractal Domain: The inherent fractal nature of HRV and RRV signals can be investigated with techniques such as the detrended fluctuation analysis (DFA), and power law analysis. These techniques will not only help in assessing signal variability, they will also help in distinguishing between physiologic and pathologic states based on the slope and intercept derived from the power law equation.

In Table 2, which follows, the variability outcomes of an exemplary study is summarized:

TABLE 2

Summary of Variability Outcomes

| Variability Outcomes | Description |
| --- | --- |
| 1. Time Domain | Standard Deviation |
| | Frequency Histograms (probability distributions) |
| 2. Frequency Domain | Fourier Frequency Spectrum Analysis |
| 3. Time-frequency Domain | Wavelet Analysis |
| 4. Scale Invariant (Fractal) Domain | Power Law Analysis |
| | Detrended Fluctuation Analysis (DFA) |
| 5. Complexity Domain | Sample Entropy (SampEn) |
| | Multiscale Entropy (MSE) |

Figure 13:
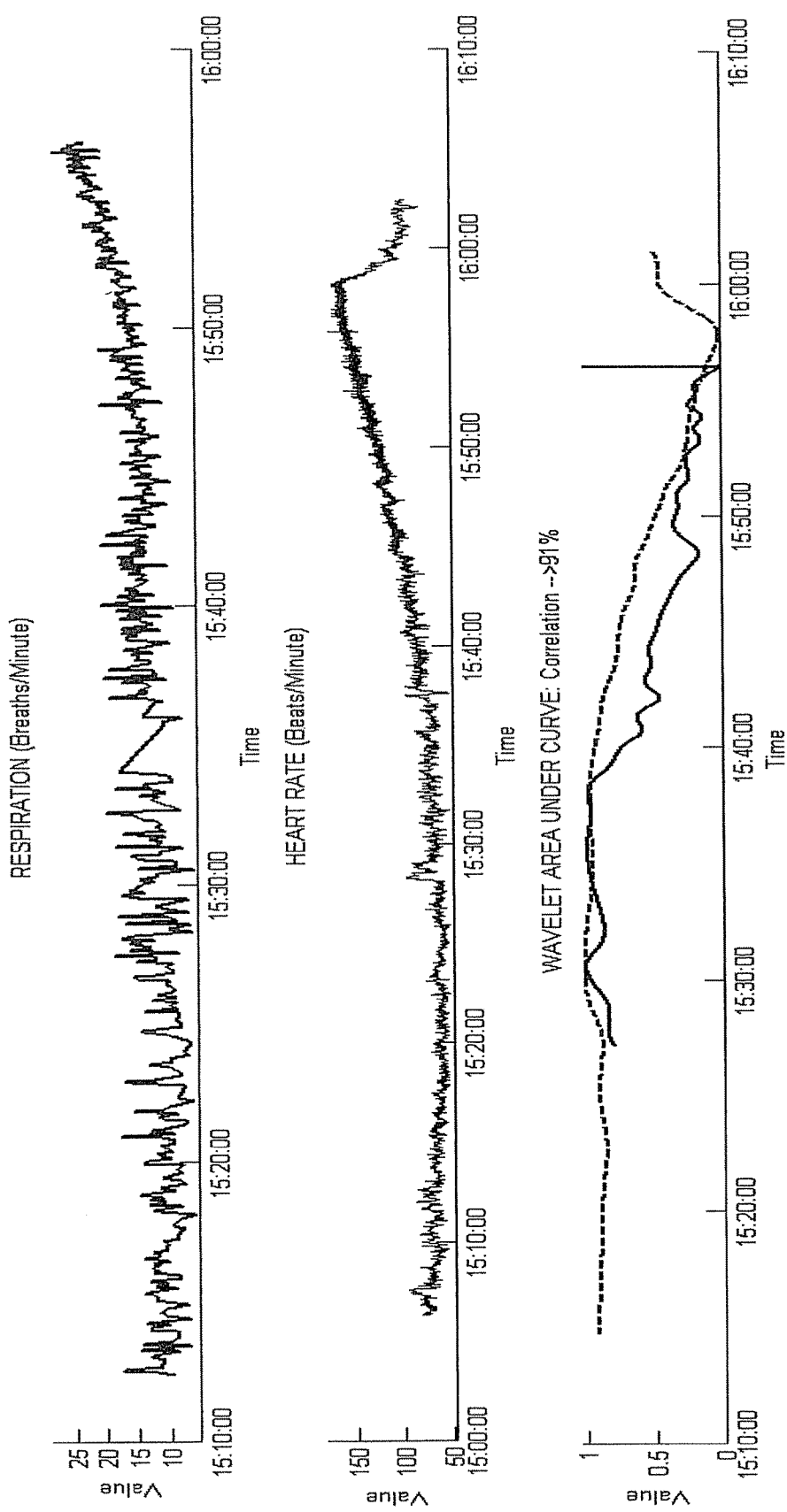
FIG. 13 is a diagram showing wavelet-based variability over time during an exercise test.
Figure 14:
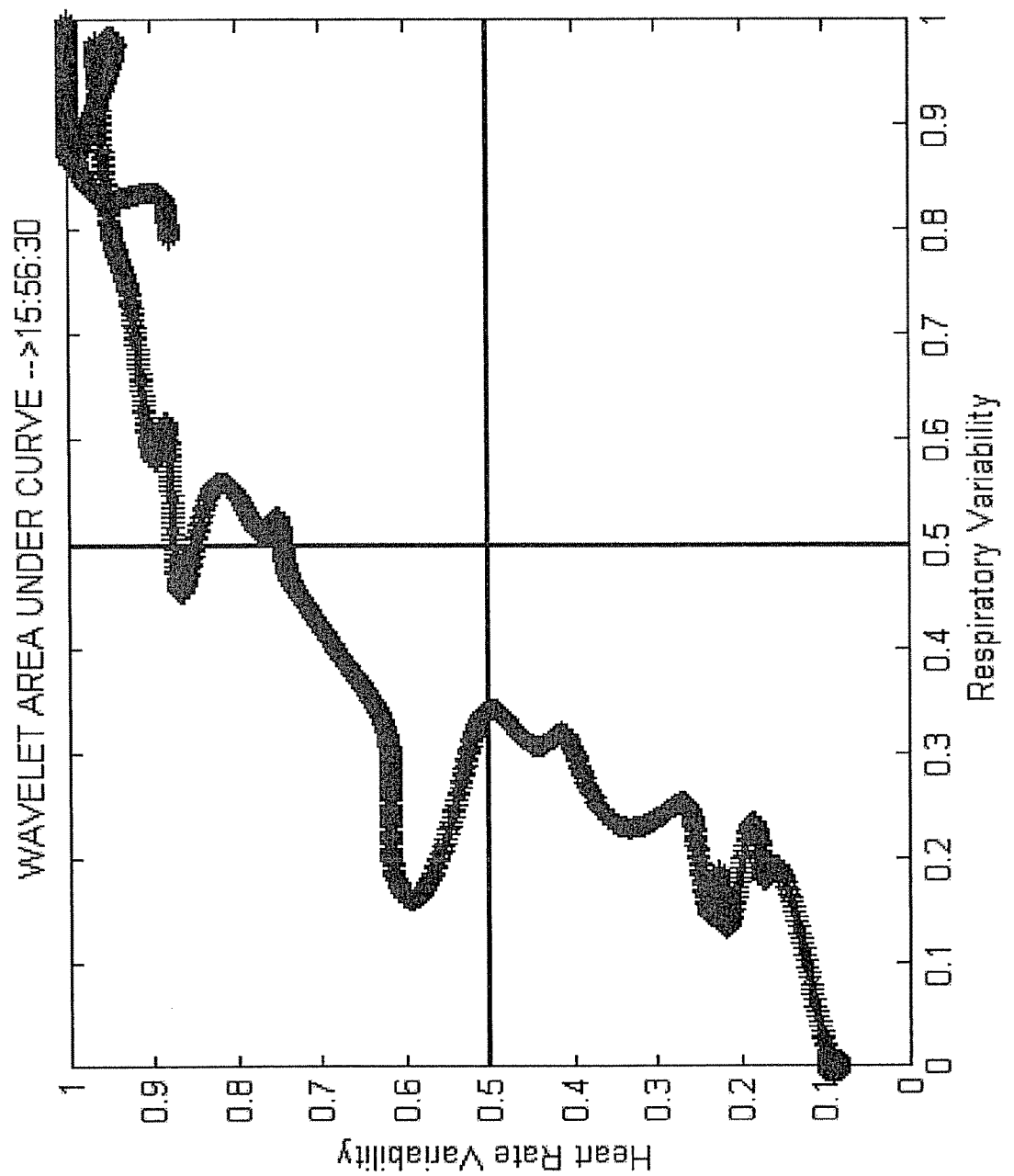
FIG. 14 is a diagram illustrating the correlation between the wavelet-based variabilities shown in FIG. 13.

Referring now to FIGS. 13 and 14, the initial results of assessing wavelet-based HRV, RRV and CPV during a first stage in an exercise test in a healthy control patient is shown. In FIG. 13, the uppermost time series shows the RR in breaths per minute, the middle time series shows HR in beats per minute, which are both measured simultaneously using sensors 30 on the same patient. It can be seen that the data in each time series is associated with a time scale. These time scales can be aligned for displaying multiple organ variability together as discussed above with respect to FIGS. 9 and 10 using standard curve fitting techniques. The lowermost time series in FIG. 13 displays the individual wavelet-based variabilities for the RR and HR signals. The solid line depicts RRV and the dotted line depicts HRV. It can be seen that there exists a correlation of approximately 91% between the wavelet-based HRV and RRV in the lowermost plot, i.e. both variability curves tend to drop simultaneously after the initiation of the stage 1 testing. FIG. 14 studies the correlation more closely by linearly regressing the HRV and RRV signals at each time point thus characterizing CPV. It can be seen in FIG. 14 that by increasing the level of exercise, the CPV drops from quadrant two (high HRV, high RRV) to quadrant four (low HRV, low RRV). The display 74 and display toolkit 72 enable the user to visualize plots such as those shown in FIGS. 13 and 14, which then provides the opportunity to explore and analyse the data in a more sophisticated and regimented manner.

Figure 15:
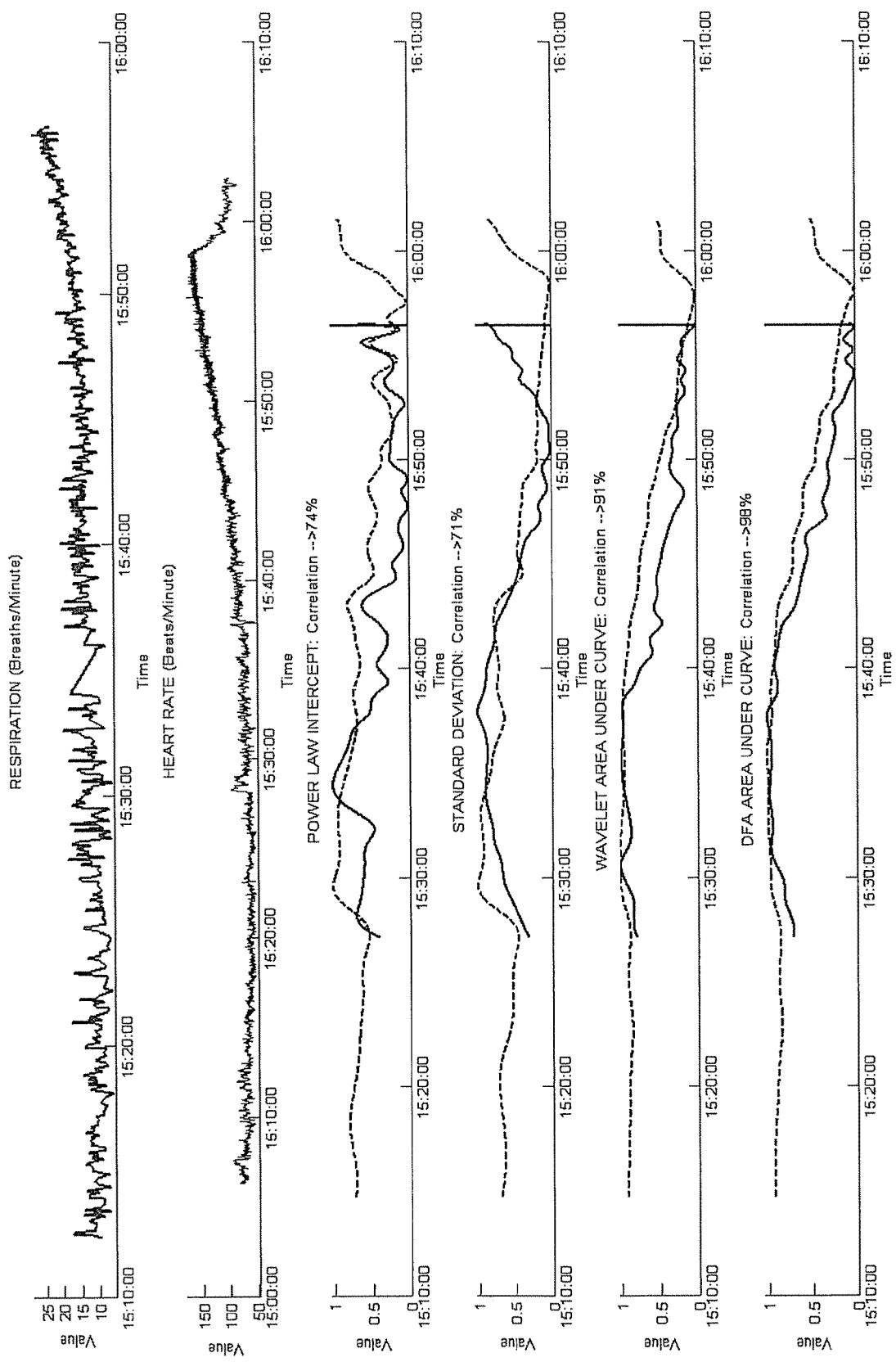
FIG. 15 shows a multi-parameter respiratory rate and heart rate variability analyses.
Figure 16:
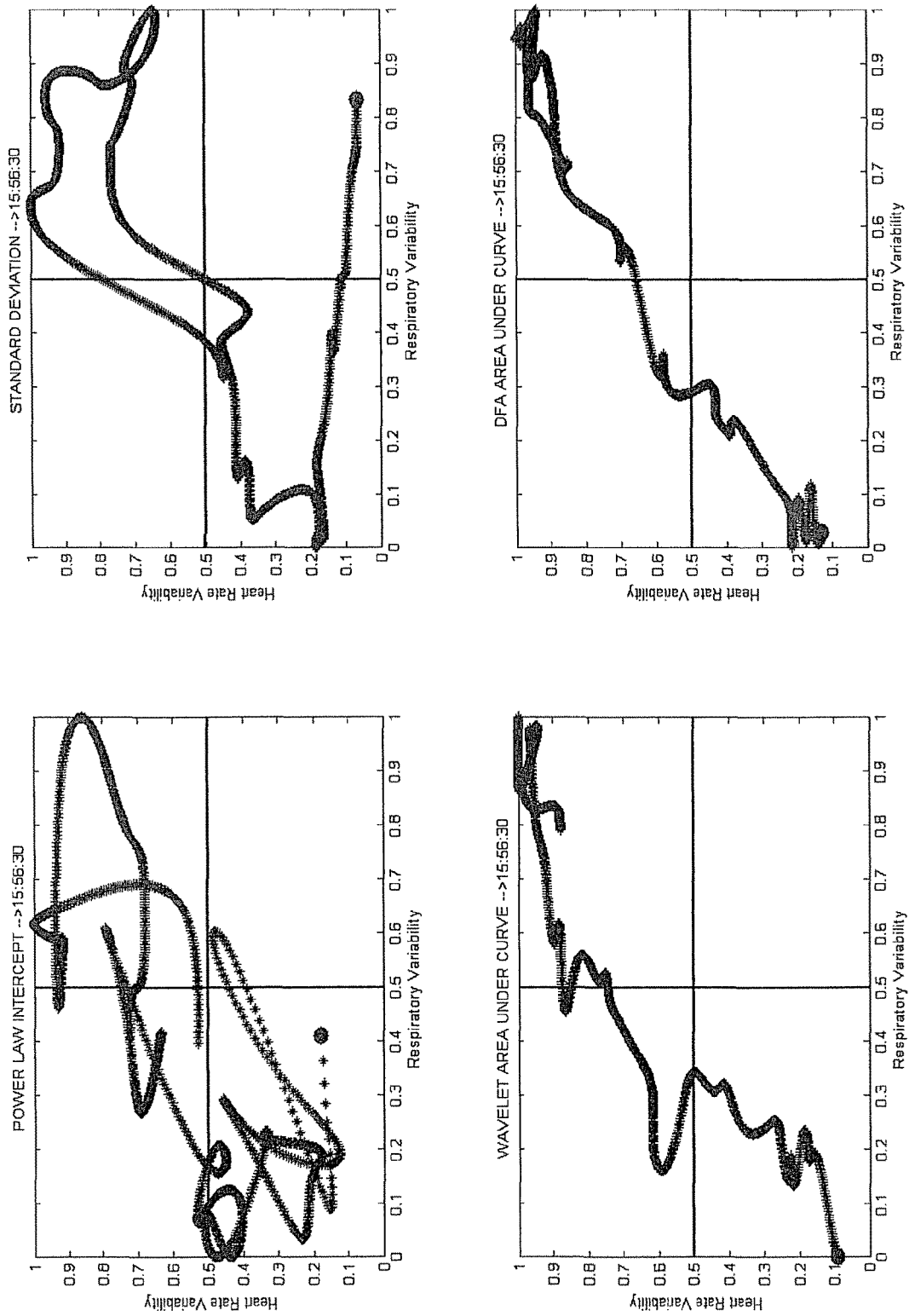
FIG. 16 shows multi-parameter multi-organ respiratory rate and heart rate variability analyses corresponding to FIG. 15.
Figure 23:
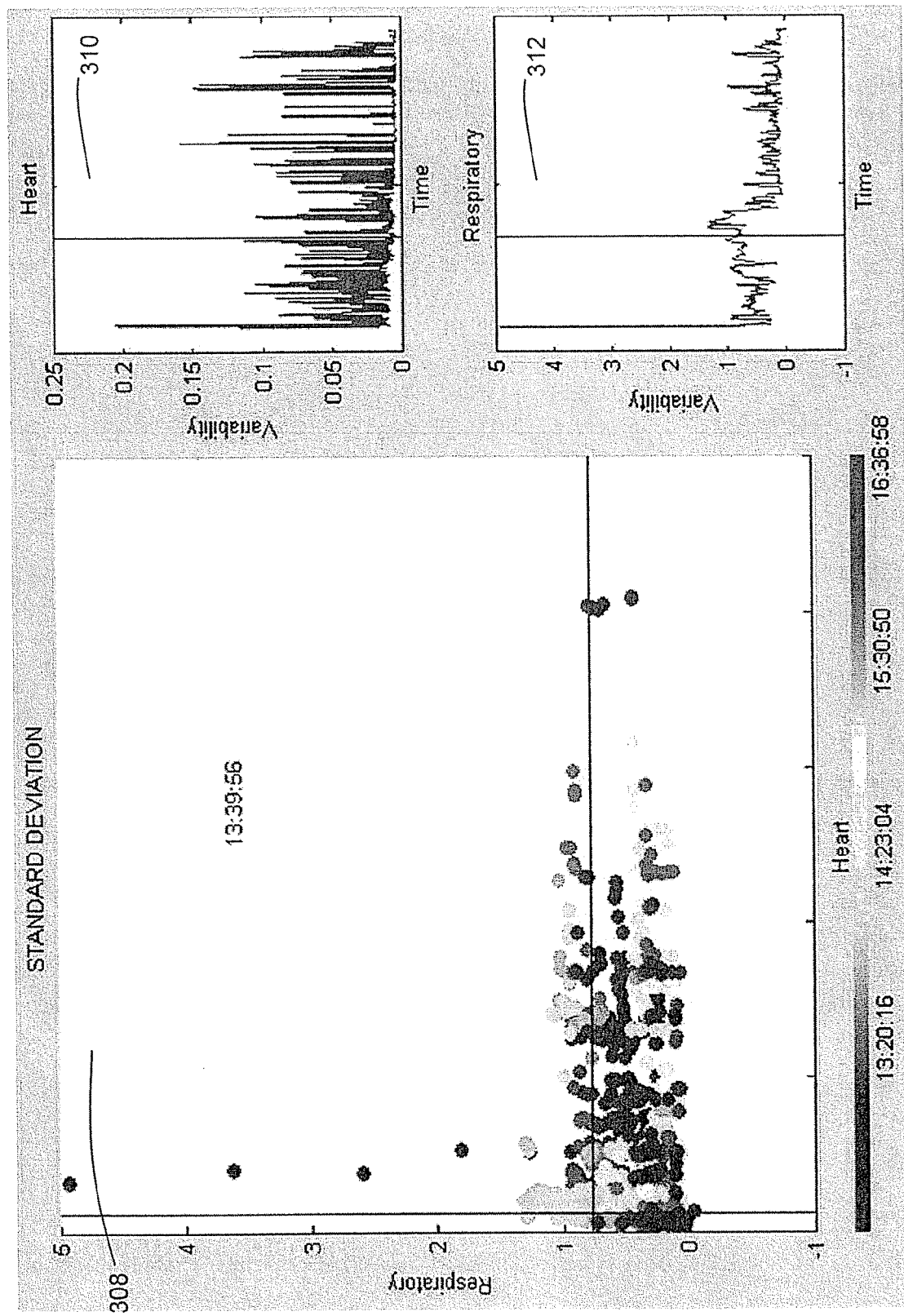
FIG. 23 is an output display showing the combination of HRV and RRV time curves to provide RRV vs. HRV trajectory curves.

FIG. 15 shows a multi-parameter RRV and HRV analysis during the same stage 1 exercise trial. In addition to the wavelet-area correlation shown in FIG. 13, FIG. 15 also provides a scale invariant power law analysis, standard deviation plot, and DFA. It can be seen that there exists a good correlation between RRV and HRV for all techniques. Again, the data packages 18 and display toolkit 72 can be used to display plots such as those shown in FIG. 15, which result from conducting the variability analyses. Such convenient display of data enables a user to better realize the correlations and significance of data from study to study and patient to patient. FIG. 16 illustrates the correlation for each statistical method by linearly regressing the HRV and RRV signals at each time point as shown in FIG. 14. It can be seen that, in general, the CPV tends to fall in a similar fashion for all statistics studied. FIG. 23 illustrates another correlation between HRV and RRV using a standard deviation trajectory curve 308, with a heart rate variability time series 310 and a respiratory variability time series 312 conveniently displayed alongside the trajectory curve 308. It may be noted that the simultaneous depiction of change in two organ variability over a time period provides an example of the visualization capabilities of the system 12, in particular for performing continuous multi-organ variability analyses.

Figure 17:
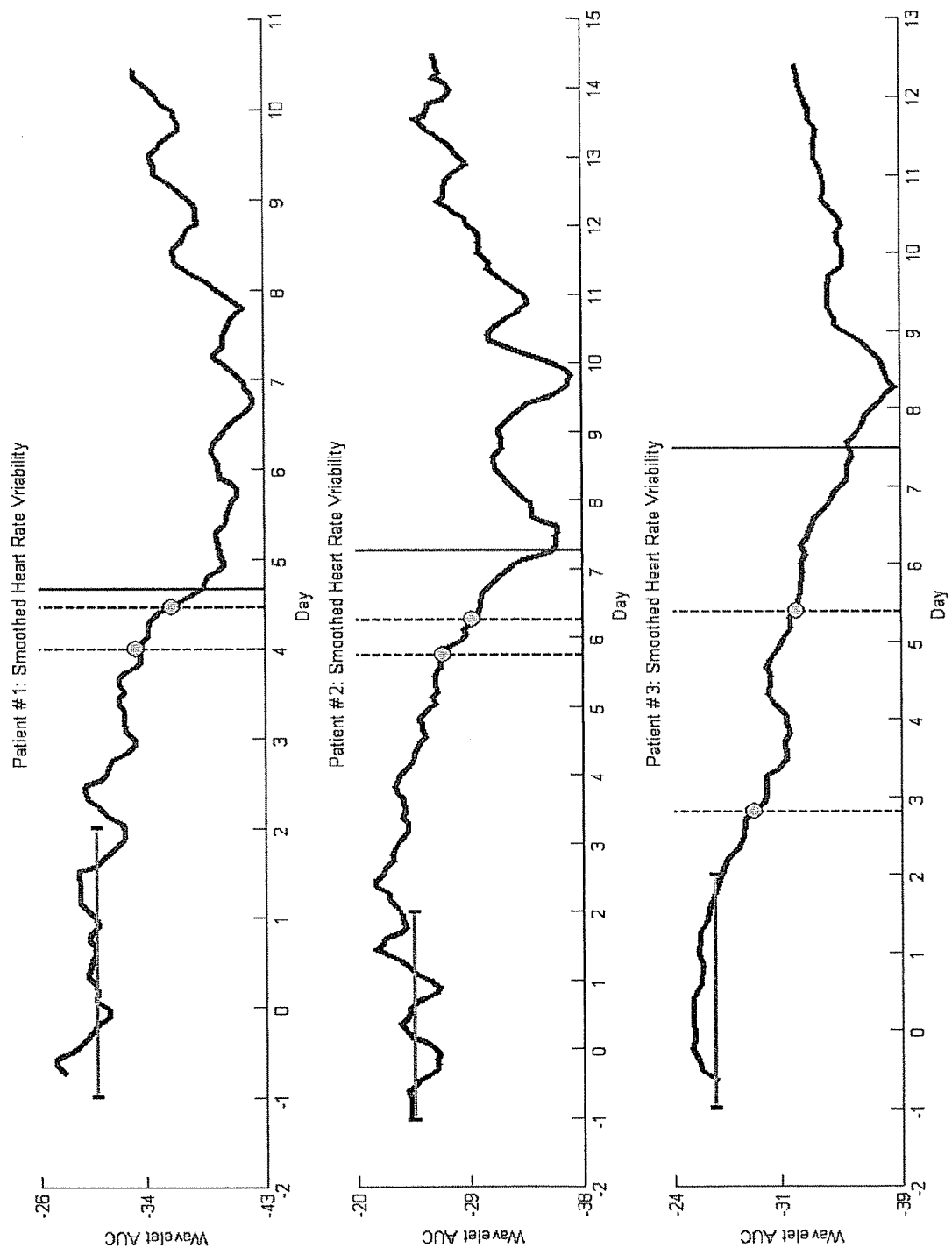
FIG. 17 shows smoothed heart rate variability for multiple patients.

As mentioned above, each variability analysis server 24 can acquire data from multiple patients in at a monitoring site 16. This enables a user (e.g. doctor) to view variability analyses conducted for multiple patients on the same display, as shown in FIG. 17. It may be noted that similar outputs can be available to users at or having access to the central service 10, given that the central service 10 has access to data packages 18 (which include the variability files 103) for many patients. This enables the threshold data 20 to be determined and refined.

In FIG. 17, a smoothed (wavelet) HRV for Patient # 1 is shown in the top time series, for Patient # 2 in the middle time series, and for Patient # 3 in the bottom time series. Baseline variability is shown by horizontal grey lines, which are the respective means of the smoothed HRV curves from day minus one to day two. A 10% drop in baseline variability is depicted by the first set of dotted vertical lines (denoted $A_1$, $A_2$, $A_3$), and the 20% drop in variability is depicted by the second set of dotted vertical lines (denoted $B_1$, $B_2$, $B_3$). The initiation of antibiotics is depicted by solid vertical lines (denoted $C_1$, $C_2$, $C_3$). For Patient # 1, a 10% drop in baseline variability occurred approximately 16 hours before the initiation of antibiotics ($A_1C_1$~16 h) and a 20% drop in baseline variability occurred approximately 5 hours before the initiation of antibiotics ($B_1C_1$~5 h). For Patient # 2, a 10% drop in baseline variability occurred approximately 36 hours before the initiation of antibiotics ($A_2C_2$~36 h) and a 20% drop in baseline variability occurred approximately 23 hours before the initiation of antibiotics ($B_2C_2$~23 h). For Patient # 3, a 10% drop in baseline variability occurred approximately 114 hours before the initiation of antibiotics ($A_3C_3$~114 h) and a 20% drop in baseline variability occurred approximately 52 hours before the initiation of antibiotics ($B_3C_3$~52 h). It can be seen that data for multiple patients can be compared and parameters such as % drop in variability identified directly from the variability data (in this case from the smooth variability data 114). The annotations shown in FIG. 17 can be made on print outs of the display output or saved directly to the variability data file 103 by providing a suitable interface device such as a touch screen or tablet. Such annotations can then be appended to the variability data file 103 to assist in later research or analysis.

Figure 22:
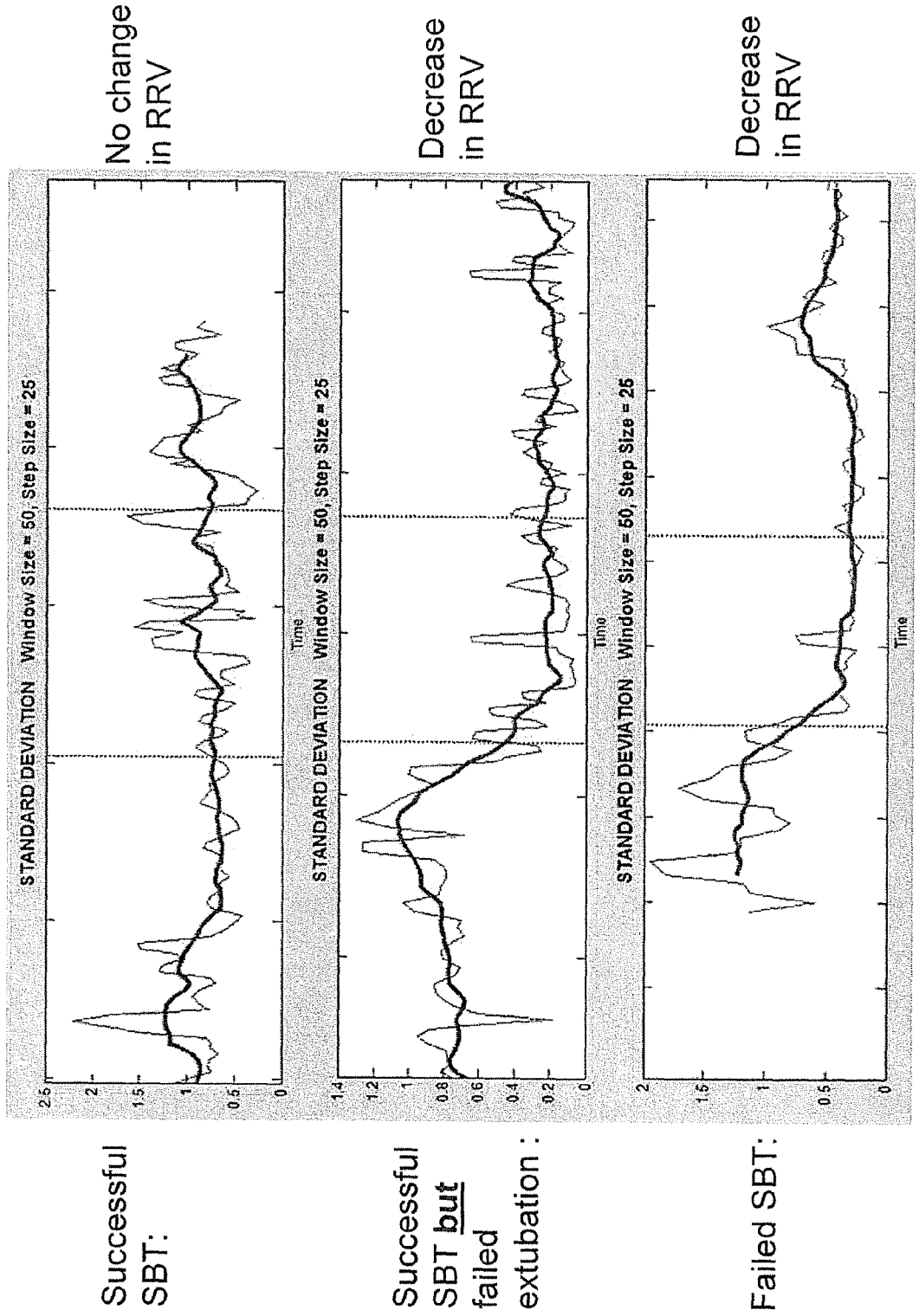
FIG. 22 shows respiratory rate variability (RRV) results for a spontaneous breath trial.

FIG. 22 illustrates an example similar to FIG. 17 but for RRV. It can be seen that in a successful spontaneous breath trial (SBT), there was no perceived change in RRV. However, in a successful SBT but failing extubation, there was a perceived decrease in RRV. It can also be seen that a failed SBT shows a decrease in RRV. Some of the clinical significance of these findings are as follows: altered variability during the SBT offers a measure of increased stress or work during a SBT, and those patients exhibiting a large change in variability during a SBT are more likely to fail extubation. These findings can also be helpful in predicting those patients who successfully liberated from mechanical ventilation, and preventing failure of extubation and the associated need for urgent re-intubation, which is in itself a life-threatening event. Moreover, isolated changes in cardiac or respiratory variability during a SBT may predict the cause of why a patient may fail extubation, and lead to preventative strategies to avoid extubation failure.

With respect to results shown in FIG. 22, it may be noted that expeditious yet safe liberation from mechanical ventilation is of critical importance in the care of the critically ill. Prolonged mechanical ventilation is associated with increased in-hospital and 5-year mortality, and elevated costs after cardiac surgery (Rajakaruna C, Rogers C A, Angelini G D, Ascione R: Risk factors for and economic implications of prolonged ventilation after cardiac surgery. *Journal of Thoracic and Cardiovascular Surgery* 2005, 130:1270-1277), and developmental delays in pediatric patients (Campbell C, Sherlock R, Jacob P, Blayney M: Congenital Myotonic Dystrophy: Assisted Ventilation Duration and Outcome. Pediatrics 2004, 113:811-816). Medical patients in the Intensive Care Unit (ICU) who require re-intubation after extubation have elevated hospital mortality rates, at least partially attributable to failed extubation (Epstein S K, Ciubotaru R L: Independent Effects of Etiology of Failure and Time to Reintubation on Outcome for Patients Failing Extubation. *American Journal of Respiratory and Critical Care Medicine* 1998, 158:489-493; Epstein S K, Ciubotaru R L, Wong J B: Effect of failed extubation on the outcome of mechanical ventilation. *Chest* 1997, 112(186-192); Epstein S K, Nevins M L, Chung J: Effect of Unplanned Extubation on Outcome of Mechanical Ventilation. *American, Journal of Respiratory and Critical Care Medicine* 2000, 161:1912-1916; and Esteban A, Alia I, Gordo F, Fernandez R, Solsona J F, I. V, S. M, M. A J, J. B, D. C. et al: Extubation outcome after spontaneous breathing trials with T-tube or pressure support ventilation. *American Journal of Respiratory and Critical Care Medicine* 1997, 156:459-465).

A number of weaning parameters have been identified and studied in order to detect readiness of a patient to be both weaned and subsequently liberated from ventilatory support (MacIntyre N R: Evidence-Based Guidelines for Weaning and Discontinuing Ventilatory Support: A Collective Task Force Facilitated by the American College of Chest Physicians; the American Association for Respiratory Care; and the American College of Critical Care Medicine. *Chest* 2000, 120:375-396). Nonetheless, the science of successful liberation from a ventilator, commonly referred to as "extubation", still remains a daily challenge, both in terms of selection of patients for extubation (who?) and identifying the appropriate time of extubation (when?).

In order to address this problem, the system 12 aims to harness hidden information contained in the dynamics of physiologic parameters to improve clinician's ability to predict extubation failure. Variability analysis documents the degree and patterns of change of physiologic parameters over intervals-in-time, and complements standard point-in-time monitoring.

Analysis of variability has been performed in isolated centers of multi-disciplinary academic excellence using disparate methods of acquiring physiologic data, differing methods to identify and remove artefact, and slightly different means to calculate variability. Currently no solution is available for clinicians interested in monitoring variability. The system 12 described herein enables such variability monitoring as discussed herein throughout.

Continuous variability monitoring provides the capacity to measure change in variability occurring as a response to an intervention or insult. For example, the change in both HRV and RRV can be evaluated as a result of a standard ICU intervention performed to assess patients' readiness for extubation, namely a spontaneous breathing trial (SBT). HRV and RRV provide a continuous measure of cardiopulmonary reserve or adaptability, and therefore, it has been found that maintaining stable cardiopulmonary variability (CPV) throughout a SBT may predict successful separation from the ventilator, and conversely, a reduction in CPV manifest during a SBT predicts extubation failure.

Figure 18:
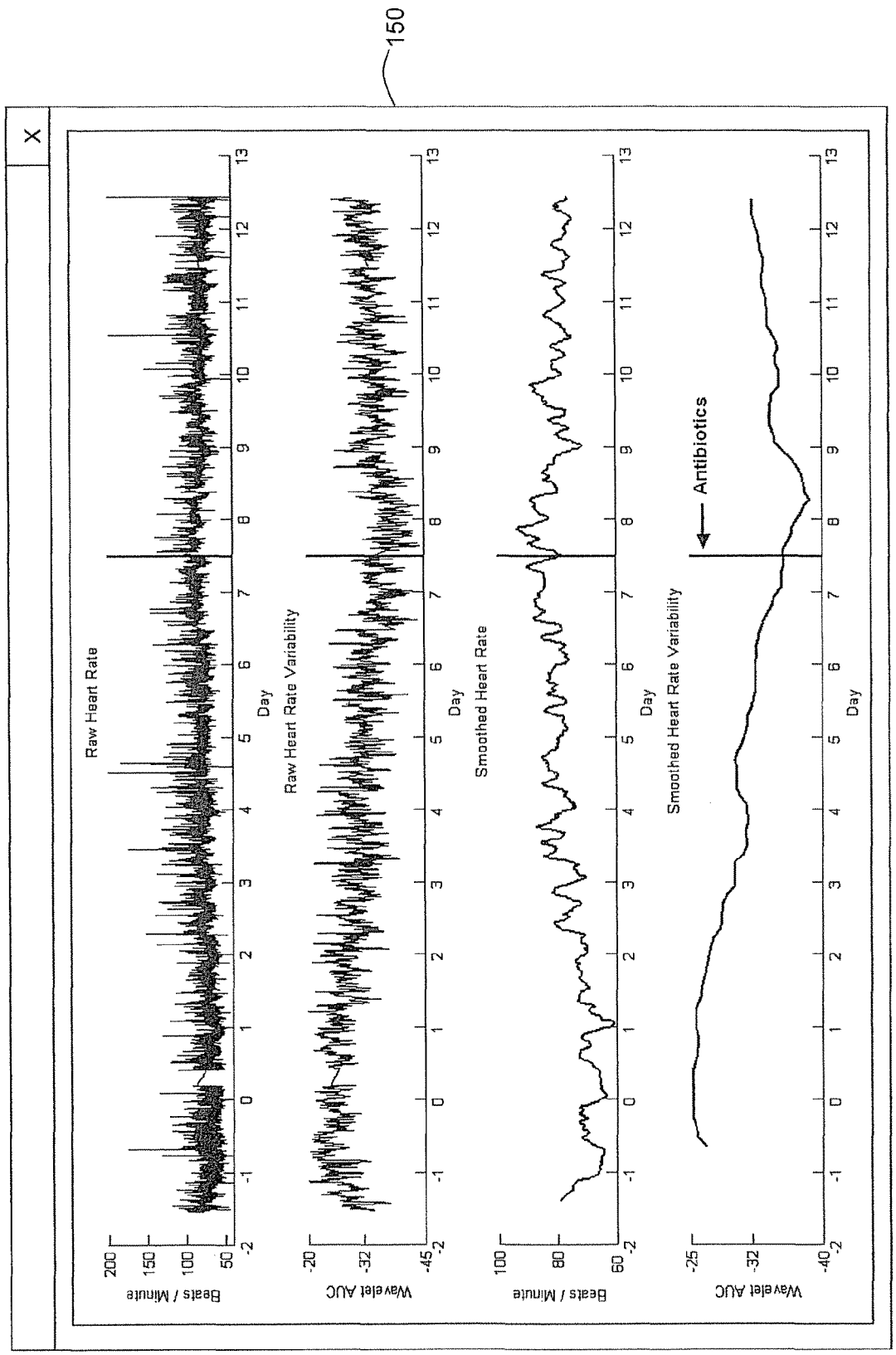
FIG. 18 shows an output display for the Vcam tool shown in FIG. 8.

As discussed above, the sensors 30 generate waveforms 62 that are stored as waveform data files 104. The waveform data 104 is then processes to generate time series, e.g. inter-breath or inter-beat time series for RR and HR respectively, which is the raw sensor data 108. These time series are then smoothed to create smooth sensor data 110. The smooth sensor data 110 can be analysed to produce the variability data 112, which can then be smoothed to produce the smooth variability data 114. FIG. 18 shows an example display generated by the Vcam tool 138, which shows a snapshot of the four types of data stored in the variability data file 103, on the same display screen 150. This enables a user to view both the raw and smooth data both before and after the variability analysis is conducted, along a common time scale. This is possible by using the time stamp data 116 which is also stored in the variability data file 103. In FIG. 18, the smooth time series are shown together at the bottom of the screen and the raw data at the top, however, it will be appreciated that the time series can be paired, i.e. raw-smooth for each, certain ones suppressed to focus on only one, or rearranged as desired by the particular user. The Vcam display 150 can be implemented in any suitable way, such as using standard display window with known and familiar functionality, or using a proprietary display interface where appropriate. Zoom and/or windowing features can also be used to focus in on a particular region in the display. It may be noted that the display interfaces, such as the displays 73 and 74 may be custom displays or may utilize commercially available equipment.

Figure 19:
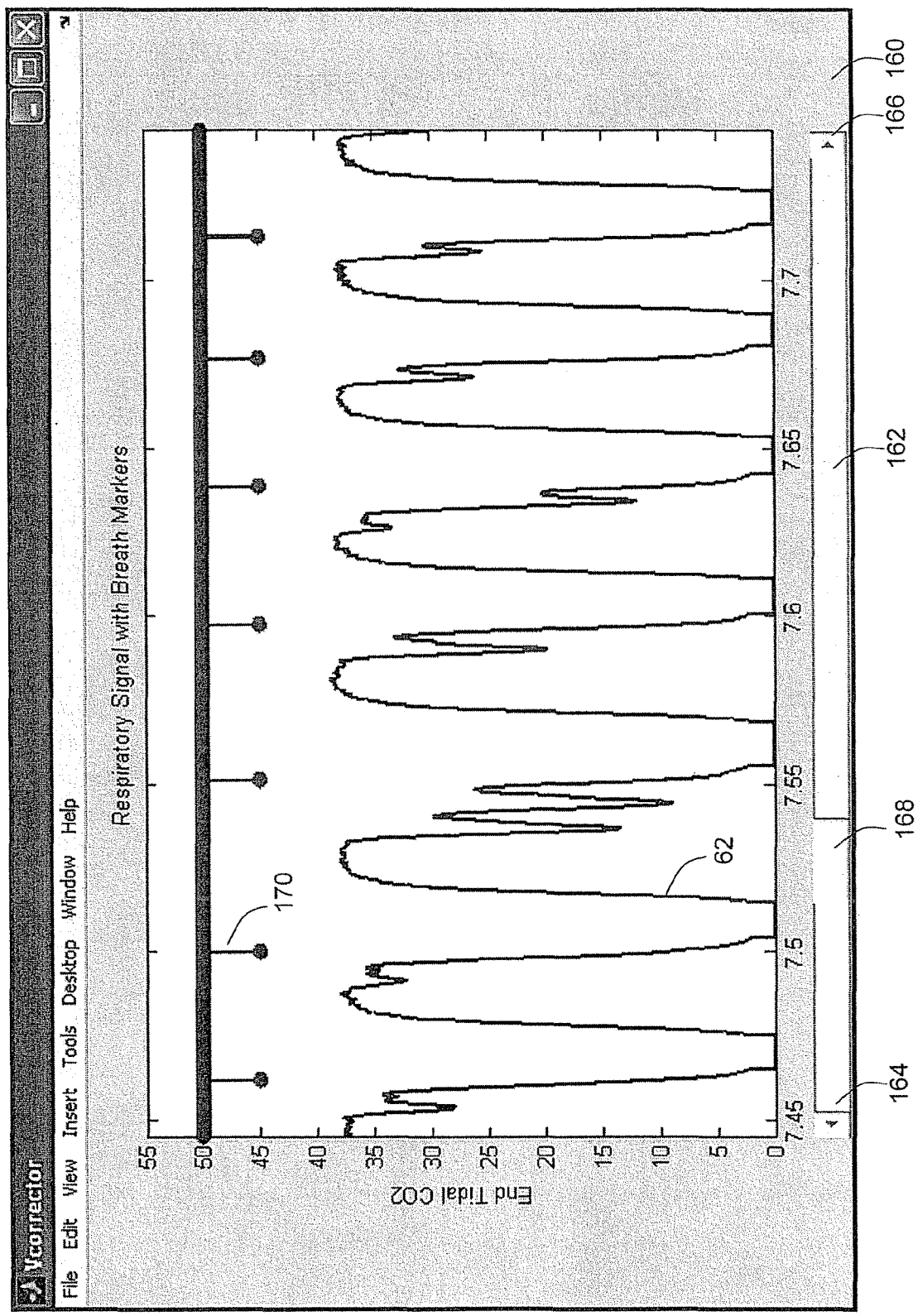
FIG. 19 shows an output display for the Vcorrector tool shown in FIG. 8.

Turning now to FIG. 19, an display screen 160 for utilizing the Vcorrector 132 tool is shown. It will be appreciated that the Vcorrector 132 can utilize the same screen 160 or interface as the other tools, such that any combination of two or more or all can be used simultaneously in the same computing environment (e.g. embedded in a single tool) for portability or modularity, or may utilize separate displays as illustrated herein. The display screen 160, includes a scrolling tool 162, which includes left and right scroll buttons 164, 166 and a scroll bar 168, commonly used in UIs. The display 160 enables the user to scroll through data, both waveform data 104 and variability data 103 over time, in both directions. This enables the user to not only look at a snapshot that is of interest, but to also look for patterns over time, or other spurious events that could be linked to certain clinical events, which, as discussed above, are stored and associated with the data packages 18 for each patient. FIG. 19 exemplifies a waveform 62 for a $CO_2$ sensor that shows end-tidal $CO_2$ readings for detecting breaths. The waveform 62 is processed using a breath detection algorithm to detect each breath and thus create the inter-breath, raw sensor data 108.

The markings 160 at the top of the waveform shows where the algorithm has detected breaths, and the user can scroll through the data to remove spurious data or otherwise incorrectly detected breaths. In one embodiment, a left-click can be used to add a breath marker, and a right-click used to delete a breath marker. The user can thus pan through the waveform data 104 and determine if the breath detection algorithm is working properly. This can be done before the raw sensor data 108 is produced, or after to generate new, corrected raw sensor data 108 in response to detection of an erroneous or suspect result. The Vcorrector tool 132 is an optional step in the overall analysis and may not be needed in certain studies. It will be appreciated that the same tools can be used to pan through the variability data stored in the variability data file 103, primarily for conducting analyses such as those depicted in FIGS. 13-17.

Figure 20:
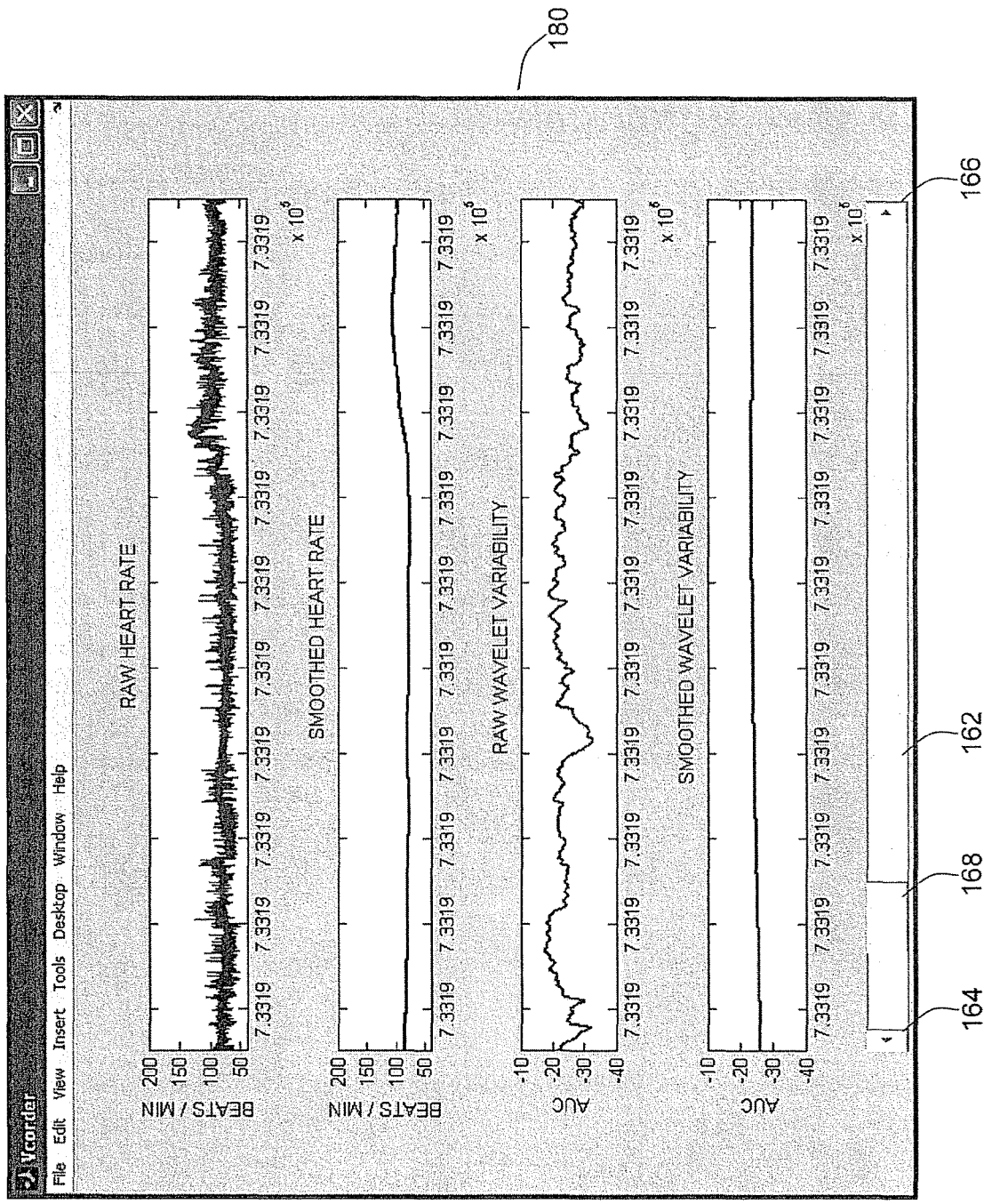
FIG. 20 shows an output display for the Vcorder tool shown in FIG. 8.

FIG. 20 shows a display screen 180 for the Vcorder tool 130. It can be seen that the Vcorder tool 130 preferably provides an output to the user which is similar to what is shown using the Vcam 128 (see FIG. 18) with the additional scroll bar 162 that is used in the Vcorrector 132. As such, the tools 128-132 can be implanted as extensions or variations of each other in a combined tool if desired with special features available for each variation. It can be seen in FIG. 20 that the Vcorder tool 130 enables the user to scroll through the data in time. In this way, for example, a user can display a series of data using the Vcam 128 then decide to look through the data over time. The Vcorder tool 130 can then be chosen which loads more data and provides the scrolling capabilities discussed above. The user may then have the option of consolidating a portion of data into a movie-like output by using the Vmovie tool 133.

Figure 21:
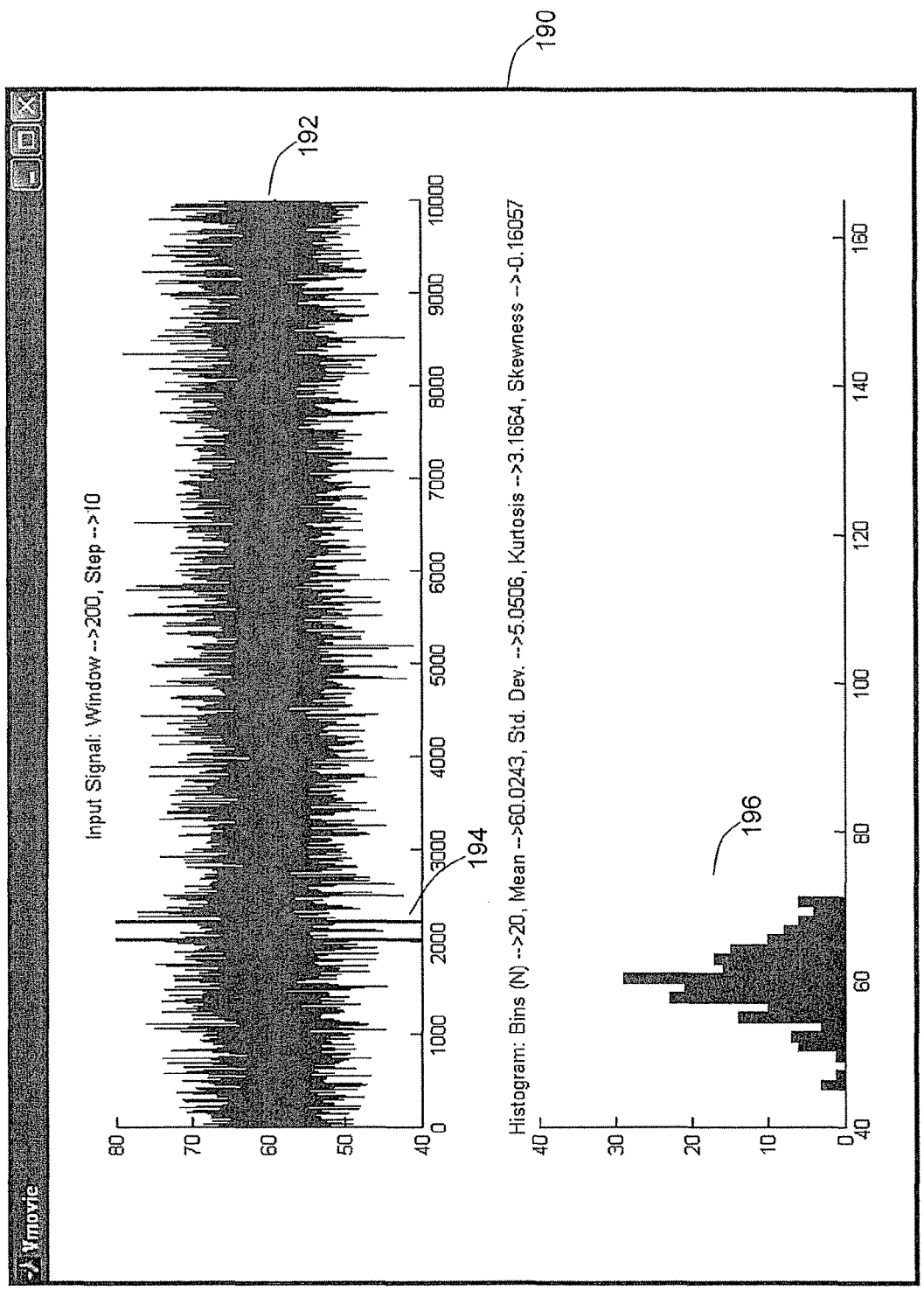
FIG. 21 shows an output display for the Vmovie tool shown in FIG. 8.

A display screen 190 for the Vmovie tool 133 is shown in FIG. 21. It can be seen that the Vmovie 133 provides a running time series 192 that shows, in this example, raw heart rate data on top with an interval marker 194 showing the interval of data that is being used for variability analysis. Below is a variability graph 196 that changes reflecting the interval that is shown above by the interval marker 194.

The screens 150, 160, 180 and 190 can optionally be provided in one application and/or consolidated display screen (not shown), which enables the user to quickly move between the different tools and have both the waveform data 104 and variability data 103 loaded and available to them at the same time. It can be appreciated that the Vmovie 133 and Vcam 128 tools are preferably provided as extensions to the Vcorder tool 130 such that a user can zoom or pan through the data, select a region and display the four plots as shown in FIG. 18 at any point in the time series or can generate movies of change in variability over time within a certain interval of time. This can be done to offer a more intuitive master tool that provides all the features in a single application for the user's convenience. The functionality of the tools in the display toolkit 72 can be upgraded and refined by having regular update data 22 sent to each server 24 at each monitoring site 16.

An example showing a typical data flow between the central service 10 and the monitoring sites 16 will now be discussed, making reference to the figures described above.

During operation, the central service 10 obtains data packages 18 from one or more monitoring sites 16 and prepares and distributes update data 22 and threshold data 20 when appropriate. The following exemplifies data flow from an ICU patient at the hospital site 16a to the central service 10 but it will be appreciated that similar principles and steps are taken by the other monitoring sites 16 as needed.

At the hospital site 16a, the ICU patient 26 is outfitted with a variety of sensors, which, in this example, obtain HR and RR data. The data acquired by the sensors 30, i.e. the waveforms, is transmitted to the patient interface 28. In this example, the patient 26 has its own patient interface 28, but it will be appreciated that shared patient interfaces can also be used. The patient interface 28 is capable of acquiring multiple organ data, which is collected by the data collection module 80. In the ICU, the waveforms 62 can be displayed for the healthcare worker on the display 73 using a local display toolkit 71. The healthcare worker uses the time stamped event recorder 82 to record clinical events that can be associated with the data acquired by the sensors 30. The data collection module 80 gathers the waveforms 62 and the time stamped event data 32 and stores the data if necessary in the data storage device 86 for later transfer to the server 24, or uses the data transfer module 88 to immediately send the data to the server 24.

As can be seen in FIG. 6, the waveforms 62 are stored in their native form in the data storage device 76 at the server 24 as well as being fed into the raw data builder 64 to create the time series used by the variability analysis module 68 for conducting variability analyses. Variability data files 103 are then built, e.g. as shown in FIG. 11, and the data conditioning module 78 amalgamates the variability data files 103 and corresponding waveform data files 104 into a combined data package 18 that is suitable to be transmitted to the central service 10.

However, as discussed above, the display toolkit 72 enables the user to correct the waveform data (e.g. breath or heart beat detection) and to view, annotate and analyse the outcome of the variability analysis in many ways. This can be done before the data package 18 is sent to the central service 10 and it will be appreciated that copies of the data packages 18 would typically be stored locally for later use. The data packages 18, when released by the user, are uploaded or sent to the central service 10. The central service 10 then receives or obtains the data packages 18 using the data collection module 90 and stores the data files in the central database 96. Once the data packages 18 are stored, they can be used, as discussed above for further research and refinement of the variability analysis techniques, thresholds and to develop upgrades to the software at the server by creating new update data 20. In this way, the data acquired from this ICU patient 26 can be compared to other patients that may be in other sites 16 in geographically spaced locations etc.

The central service 10 can, at any time, either periodically or on a need-to basis, prepare and distribute threshold data 20 and update data 22 according to the discussion above. It will be appreciated that the data 20, 22 can be pushed to the monitoring sites 16 or pulled down using any suitable and known data transfer mechanism and should not be limited to any particular one. Similarly, the research programs 94 and statistics engine 100 can be utilized "off-line" or can be regimented to conduct regular refinements or data mining sessions. The administration interface 92 can also be used periodically or on a need-to basis. The update data 22 and threshold data 20 can be built manually, automatically using prepared algorithms or a combination of both. The connectivity provided by the system 12 also provides a framework for sending alerts between monitoring sites, e.g. by way of emails. This may be useful where outpatients move from a hospital site 16a to a clinic site 16b or mobile site 16c and information should be shared with a regular practitioner.

The data flows above may be done in real time or at any interval that suits the particular application and environment. In this way, regular monitoring can be done at the site and alerts created locally, which are then added as appended data to data packages 18 for a particular patient, which are then uploaded or transmitted in bulk exchanges. This enables the data packages 18 to be analysed locally and annotated when appropriate rather then immediately sending data directly to the central service 10. However, if a particular environment does not have local monitoring, e.g. certain mobile sites, the central service 10 can be used to either do the monitoring or redirect data to an appropriate monitoring centre (similar to the arrangement in a clinic site 16*b*).

It can therefore be seen that the underlying theory behind variability analysis over time has a widespread application in many environments, e.g. for treatment, early diagnosis, real-time prognosis and overall health monitoring. In order to take advantage of the power of variability analysis, the underlying framework described above can handle variability analyses across a distributed system in a consistent manner, in part by constructing a standard variability data file that includes several manifestations of the underlying data acquired using variability monitoring over time. The consistent and standard data files, along with the underlying framework enables a user to make use of a set of convenient display tools, while a central entity can provide connectivity to the distributed environment and provide a way to update the equipment and software to ensure consistent and relevant analyses. The system can be extended into many environments, including in-patient, out-patient and completely mobile/stand-alone.

Although the invention has been described with reference to certain specific embodiments, various modifications thereof will be apparent to those skilled in the art without departing from the spirit and scope of the invention as outlined in the claims appended hereto.

The invention claimed is:

1. A method for enabling variability analyses conducted over time at a plurality of sites to be interpreted, said method comprising:
providing a connection between a central service and at least a first site of said plurality of sites;
said central service obtaining from said first site, a data package comprising variability data and at least one clinical event associated with said variability data, said variability data having been generated at said first site from a variability analysis conducted over time based on sensor data acquired from at least one patient interface, said variability analysis comprising computing a measure of variability for a plurality of time intervals for at least one parameter, each measure of variability indicative of a degree and character to which a respective parameter changes over an interval of time, said at least one clinical event having been recorded at said first site during acquisition of said sensor data, each clinical event being time stamped to enable said clinical event to be associated with corresponding times at which said variability analysis was performed, each clinical event having been recorded independently of said variability analysis;
said central service storing said data package in a central database configured to store a plurality of data packages, and making said database available for further processing;
said central service enabling said clinical event data to be compared to associated variability data in at least one of said plurality of data packages to enable said variability data to be interpreted in connection with said at least one clinical event at said corresponding times; and
said central service providing feedback to at least one of said plurality of sites based on an analysis interpreting variability using said plurality of data packages in said central database.

2. A method for enabling variability analyses to be interpreted, said method comprising a processor at a monitoring site:
obtaining variability data generated from a variability analysis conducted over time based on sensor data acquired from at least one patient interface, said variability analysis comprising computing a measure of variability for a plurality of time intervals for at least one parameter, each measure of variability indicative of a degree and character to which a respective parameter changes over an interval of time;
enabling clinical events to be recorded independently of acquisition of said sensor data used to conduct said variability analysis;
obtaining at least one clinical event recorded during acquisition of said sensor data, each clinical event being time stamped to enable said clinical event to be associated with corresponding times at which said variability analysis was performed, each clinical event being recorded independently of said variability analysis;
associating said at least one clinical event with said variability analysis to enable said variability data to be interpreted in connection with said at least one clinical event at said corresponding times; and
outputting said variability data and said at least one clinical event with an indication of said association therebetween.

3. A method for preparing a data package representing results of variability analyses conducted at a respective site, said method comprising a processor at a monitoring site:
obtaining a waveform for a physiological parameter over a period of time comprising a plurality of time intervals, said waveform having been acquired from at least one patient interface configured to obtain data from at least one sensor;
using said waveform to obtain raw sensor data comprising a raw time series;
smoothing said raw sensor data to obtain smooth sensor data;
using said smooth sensor data to conduct a variability analysis to obtain raw variability data, said variability analysis comprising computing a measure of variability for said plurality of time intervals for at least said physiological parameter, each measure of variability indicative of a degree and character to which a respective parameter changes over an interval of time;
smoothing said raw variability data to obtain smooth variability data;
associating time stamp data with said raw sensor data, said smooth sensor data, said raw variability data, and said smooth variability data;
generating a variability data file using said raw sensor data, said smooth sensor data, said raw variability data, said smooth variability data, and said time stamp data;
obtaining at least one clinical event recorded during acquisition of said waveform, each clinical event being time stamped to enable said clinical event to be associated with corresponding times at which said variability analysis was performed, each clinical event having been recorded independently of said variability analysis;
adding clinical event data corresponding to said at least one clinical event to said variability data file to enable said variability data to be interpreted in connection with said at least one clinical event at said corresponding times; and
including said variability data file in said data package.

4. The method according to claim 2, further comprising:
establishing a connection between a site configured to perform said method and a central service configured to obtain and store variability data and associated clinical events obtained from a plurality of sites;

preparing a data package comprising at least a first data file, said first data file comprising said variability data and said at least one clinical event; and providing said data package available to said central service to enable said central service to store said data package with other data packages in a central database and to make said database available for further processing.

5. The method according to claim 4 wherein said clinical events are recorded by said at least one patient interface concurrently with said sensor data.

6. The method according to claim 4 wherein said clinical events are recorded automatically by detecting external events.

7. The method according to claim 4 wherein said clinical events are recorded using an event recorder having a display to enable a user to manually record said clinical events as they are detected.

8. A system for enabling variability analyses to be interpreted, said system comprising a processor, memory, and at least one connection configured to obtain variability data and clinical events, said memory storing computer executable instructions for operating said processor to:

obtain variability data generated from a variability analysis conducted over time based on sensor data acquired from at least one patient interface, said variability analysis comprising computing a measure of variability for a plurality of time intervals for at least one parameter, each measure of variability indicative of a degree and character to which a respective parameter changes over an interval of time;

enable clinical events to be recorded independently of acquisition of said sensor data used to conduct said variability analysis;

obtain at least one clinical event recorded during acquisition of said sensor data, each clinical event being time stamped to enable said clinical event to be associated with corresponding times at which said variability analysis was performed, each clinical event being recorded independently of said variability analysis;

associate said at least one clinical event with said variability analysis to enable said variability data to be interpreted in connection with said at least one clinical event at said corresponding times; and output said variability data and said at least one clinical event with an indication of said association therebetween.

9. The system according to claim 8 wherein said clinical events are recorded by said at least one patient interface concurrently with said sensor data.

10. The system according to claim 8 wherein said clinical events are recorded automatically by detecting external events.

11. The system according to claim 8 wherein said clinical events are recorded using an event recorder having a display to enable a user to manually record said clinical events as they are detected.

12. The method according to claim 2, further comprising:

obtaining from said central service, threshold data comprising information pertaining to parameters of variability analyses capable of being conducted at said site, said threshold data being derived from contents of said central database; and obtaining from said central service, update data comprising information for maintaining consistency of said site with others of said plurality of sites.

13. The method according to claim 12 wherein said threshold data comprises information pertaining to thresholds to be used by said plurality of sites when conducting said variability analyses, said thresholds configured to be used to trigger one or more alerts.

14. The method according to claim 2 wherein said site is a hospital site comprising at least one variability analysis server connected to at least one patient interface, each patient interface connected to at least one sensor for measuring a respective parameter of a patient; and one or more additional interfaces to existing systems within said hospital site.

15. The method according to claim 2 wherein said site is a a clinic site comprising at least one variability analysis server connected to at least one patient interface, each patient interface connected to at least one sensor for measuring a respective parameter of a patient; and a monitoring centre connected to said at least one variability analysis server.

16. The method according to claim 2 wherein said site is a mobile site comprising at least one variability analysis server connected to at least one patient interface, each patient interface connected to at least one sensor for measuring a respective parameter of a patient; wherein said analysis server and said patient interface are hosted by a mobile device.

17. The method according to claim 2 wherein said central service is remote from said site, and said data packages are either pushed to said central service or pulled from said central service.

18. The method according to claim 12 wherein said threshold data and said update data are either pushed to said site or pulled from said central service.

19. The method according to claim 12, wherein said update data comprises upgrades to software running at said plurality of sites.

20. The method according to claim 4, wherein said variability data and said at least one clinical event are output in a data package, said data package being generated by:

obtaining a waveform for a parameter over a period of time comprising said plurality of time intervals;

using said waveform to obtain raw sensor data comprising a raw time series;

smoothing said raw sensor data to obtain smooth sensor data;

using said smooth sensor data to conduct said variability analysis to obtain raw variability data;

smoothing said raw variability data to obtain smooth variability data;

associating time stamp data with said raw sensor data, said smooth sensor data, said raw variability data, and said smooth variability data;

generating a variability data file using said raw sensor data, said smooth sensor data, said raw variability data, said smooth variability data, and said time stamp data;

adding clinical event data corresponding to said at least one clinical event to said variability data file; and including said variability data file in said data package.

21. The method according to claim 20, further comprising appending additional data relevant to said variability analysis.

22. The method according to claim 21, wherein said additional data comprises patient data.

23. The system according to claim 8, further comprising computer executable instructions for operating the processor to:

establish a connection between a site associated with said system and a central service configured to obtain and store variability data and associated clinical events obtained from a plurality of sites;

prepare a data package comprising at least a first data file, said first data file comprising said variability data and said at least one clinical event; and provide said data package available to said central service to enable said central service to store said data package with other data packages in a central database and to make said database available for further processing.

24. The system according to claim 23, further comprising computer executable instructions for operating the processor to:

obtain from said central service, threshold data comprising information pertaining to parameters of variability analyses capable of being conducted at said site, said threshold data being derived from contents of said central database; and obtain from said central service, update data comprising information for maintaining consistency of said site with others of said plurality of sites.

25. The system according to claim 24 wherein said threshold data comprises information pertaining to thresholds to be used by said plurality of sites when conducting said variability analyses, said thresholds configured to be used to trigger one or more alerts.

26. The system according to claim 23 wherein said site is a hospital site and said system further comprises at least one variability analysis server connected to at least one patient interface, each patient interface connected to at least one sensor for measuring a respective parameter of a patient; and one or more additional interfaces to existing systems within said hospital site.

27. The system according to claim 23 wherein said site is a a clinic site and said system comprises at least one variability analysis server connected to at least one patient interface, each patient interface connected to at least one sensor for measuring a respective parameter of a patient; and a monitoring center connected to said at least one variability analysis server.

28. The system according to claim 23 wherein said site is a mobile site and said system comprises at least one variability analysis server connected to at least one patient interface, each patient interface connected to at least one sensor for measuring a respective parameter of a patient; wherein said system is hosted by a mobile device.

29. The system according to claim 24, wherein said central service is remote from said site, and said data packages are either pushed to said central service or pulled from said central service.

30. The system according to claim 24 wherein said threshold data and said update data are either pushed to said site or pulled from said central service.

31. The system according to claim 24, wherein said update data comprises upgrades to software running at said plurality of sites.

32. The system according to claim 8, wherein said variability data and said at least one clinical event are output in a data package, said data package being generated by:

obtaining a waveform for a parameter over a period of time comprising said plurality of time intervals;

using said waveform to obtain raw sensor data comprising a raw time series;

smoothing said raw sensor data to obtain smooth sensor data;

using said smooth sensor data to conduct said variability analysis to obtain raw variability data;

smoothing said raw variability data to obtain smooth variability data;

associating time stamp data with said raw sensor data, said smooth sensor data, said raw variability data, and said smooth variability data;

generating a variability data file using said raw sensor data, said smooth sensor data, said raw variability data, said smooth variability data, and said time stamp data;

adding clinical event data corresponding to said at least one clinical event to said variability data file; and including said variability data file in said data package.

33. The system according to claim 32, further comprising computer executable instructions for appending additional data relevant to said variability analysis.

34. The system according to claim 33, wherein said additional data comprises patient data.

35. The method according to claim 3, further comprising sending said data package to a central service configured to obtain and store variability data and associated clinical events obtained from a plurality of sites.

36. The method according to claim 3, further comprising appending additional data relevant to said variability analysis.

37. The method according to claim 36, wherein said additional data comprises patient data.

38. A system for preparing a data package representing results of variability analyses conducted at a respective site, said system comprising a processor, memory, and at least one connection configured to obtain variability data and clinical events, said memory storing computer executable instructions for operating the processor to:

obtain a waveform for a physiological parameter over a period of time comprising a plurality of time intervals, said waveform having been acquired from at least one patient interface configured to obtain data from at least one sensor;

use said waveform to obtain raw sensor data comprising a raw time series;

smooth said raw sensor data to obtain smooth sensor data;

use said smooth sensor data to conduct a variability analysis to obtain raw variability data, said variability analysis comprising computing a measure of variability for said plurality of time intervals for at least said physiological parameter, each measure of variability indicative of a degree and character to which a respective parameter changes over an interval of time;

smooth said raw variability data to obtain smooth variability data;

associate time stamp data with said raw sensor data, said smooth sensor data, said raw variability data, and said smooth variability data;

generate a variability data file using said raw sensor data, said smooth sensor data, said raw variability data, said smooth variability data, and said time stamp data;

obtain at least one clinical event recorded during acquisition of said waveform, each clinical event being time stamped to enable said clinical event to be associated with corresponding times at which said variability analysis was performed, each clinical event having been recorded independently of said variability analysis;

add clinical event data corresponding to said at least one clinical event to said variability data file to enable said variability data to be interpreted in connection with said at least one clinical event at said corresponding times; and include said variability data file in said data package.

39. The system according to claim 38, further comprising computer executable instructions for operating the processor to send said data package to a central service configured to obtain and store variability data and associated clinical events obtained from a plurality of sites.

40. The system according to claim 38, further comprising computer executable instructions for operating the processor to append additional data relevant to said variability analysis.

41. The system according to claim 40, wherein said additional data comprises patient data.

42. The method according to claim 1, wherein said feedback comprises threshold data comprising information pertaining to parameters of variability analyses capable of being conducted at said plurality of sites, said threshold data being derived from contents of said central database.

43. The method according to claim 42, wherein said threshold data comprises information pertaining to thresholds to be used by said plurality of sites when conducting said variability analyses, said thresholds configured to be used to trigger one or more alerts.

44. The method according to claim 1, wherein said feedback comprises update data comprising information for maintaining consistency of said plurality of sites.

45. A system for enabling variability analyses conducted over time at a plurality of sites to be interpreted, said system comprising a processor, memory, and at least one connection configured to communicate with said plurality of sites, said memory storing computer executable instructions for operating the processor to:

provide a connection between said system and at least a first site of said plurality of sites;

obtain from said first site, a data package comprising variability data and at least one clinical event associated with said variability data, said variability data having been generated at said first site from a variability analysis conducted over time based on sensor data acquired from at least one patient interface, said variability analysis comprising computing a measure of variability for a plurality of time intervals for at least one parameter, each measure of variability indicative of a degree and character to which a respective parameter changes over an interval of time, said at least one clinical event having been recorded at said first site during acquisition of said sensor data, each clinical event being time stamped to enable said clinical event to be associated with corresponding times at which said variability analysis was performed, each clinical event having been recorded independently of said variability analysis;

store said data package in a central database configured to store a plurality of data packages, and making said database available for further processing;

enable said clinical event data to be compared to associated variability data in at least one of said plurality of data packages to enable said variability data to be interpreted in connection with said at least one clinical event at said corresponding times; and provide feedback to at least one of said plurality of sites based on an analysis interpreting variability using said plurality of data packages in said central database.

46. The system according to claim 45, wherein said feedback comprises threshold data comprising information pertaining to parameters of variability analyses capable of being conducted at said plurality of sites, said threshold data being derived from contents of said central database.

47. The system according to claim 46, wherein said threshold data comprises information pertaining to thresholds to be used by said plurality of sites when conducting said variability analyses, said thresholds configured to be used to trigger one or more alerts.

48. The system according to claim 45, wherein said feedback comprises update data comprising information for maintaining consistency of said plurality of sites.

* * * * *